United States Patent
Wang et al.

(12)

(10) Patent No.: US 11,513,071 B2
(45) Date of Patent: Nov. 29, 2022

(54) SENSING DEVICE FOR DETECTING ANALYTE CONTAINING NON-METALLIC ELEMENT, AND METHOD THEREOF

(71) Applicants: Qingwu Wang, Chelmsford, MA (US); Sajjad Maruf, San Marcos, CA (US); Jirui Wang, Lowell, MA (US)

(72) Inventors: Qingwu Wang, Chelmsford, MA (US); Sajjad Maruf, San Marcos, CA (US); Jirui Wang, Lowell, MA (US)

(73) Assignee: 2WITECH SOLUTIONS LLC, Lowell, MA (US)

( * ) Notice: Subject to any disclaimer, the term of this patent is extended or adjusted under 35 U.S.C. 154(b) by 383 days.

(21) Appl. No.: 16/746,789

(22) Filed: Jan. 17, 2020

(65) Prior Publication Data
US 2021/0109018 A1    Apr. 15, 2021

Related U.S. Application Data

(60) Provisional application No. 62/973,591, filed on Oct. 15, 2019.

(51) Int. Cl.
*G01N 21/47* (2006.01)
*G01N 21/59* (2006.01)
(Continued)

(52) U.S. Cl.
CPC ....... *G01N 21/4788* (2013.01); *C08F 220/06* (2013.01); *G01N 21/59* (2013.01);
(Continued)

(58) Field of Classification Search
CPC .............. G01N 21/4788; G01N 21/59; G01N 33/54373; G01N 21/78; G01N 2021/7723;
(Continued)

(56) References Cited

U.S. PATENT DOCUMENTS

2011/0079075 A1 * 4/2011 Zheng .................. G01N 27/126
    73/38
2011/0262306 A1 * 10/2011 Hsu ....................... B01J 20/268
    422/69

FOREIGN PATENT DOCUMENTS

WO    WO-2018231962 A1 * 12/2018 ............ B01J 20/268

OTHER PUBLICATIONS

Wu et al., "Direct and label-free detection of cholic acid based on molecularly imprinted photonic hydrogels", 2008, Journal of Materials Chemistry, 18, 5452-5458 (Year: 2008).*
(Continued)

*Primary Examiner* — Samuel P Siefke
*Assistant Examiner* — Henry H Nguyen
(74) *Attorney, Agent, or Firm* — George Guosheng Wang; Upstream Research and Patent LLC

(57) ABSTRACT

The present invention provides a sensing device for detecting an analyte containing a non-metallic element such as F. A working sensor has a 3D array of voids each having a void internal wall. The void internal walls have cavities each having a cavity internal wall made from a material containing the non-metallic element. A binding of the analytes to the cavities induces a detectable variation of the optical property of the 3D array of voids. The invention exhibits numerous technical merits such as high sensitivity, high specificity, fast detection, ease of operation, low power consumption, zero chemical release, and low operation cost, among others.

18 Claims, 21 Drawing Sheets

(51) Int. Cl.
*C08F 220/06* (2006.01)
*G02B 1/00* (2006.01)
*G01N 33/543* (2006.01)
*B82Y 15/00* (2011.01)
*B82Y 20/00* (2011.01)
*B01J 20/26* (2006.01)
*B01J 35/10* (2006.01)

(52) U.S. Cl.
CPC ....... *G01N 33/54373* (2013.01); *G02B 1/005* (2013.01); *B01J 20/268* (2013.01); *B01J 35/10* (2013.01); *B82Y 15/00* (2013.01); *B82Y 20/00* (2013.01)

(58) Field of Classification Search
CPC .......... G01N 2021/7776; C08F 220/06; C08F 220/24; G02B 1/005; G02B 2207/107; B01J 20/268; B01J 35/10; B82Y 15/00; B82Y 20/00; B82Y 30/00
See application file for complete search history.

(56) References Cited

OTHER PUBLICATIONS

Cennamo et al., "A Molecularly Imprinted Polymer on a Plasmonic Plastic Optical Fiber to Detect Perfluorinated Compounds in Water", Jun. 2018, Sensors, 18, 1836 (Year: 2018).*
Wang et al., "Cellulose photonic crystal film sensor for alcohols", 2015, Sensors and Actuators B 220, 222-226 (Year: 2015).*
Li et al., Rapid detection of sulfaguanidine in fish by using a photonic crystal molecularly imprinted polymer, May 2019, Food Chemistry 281, 57-62 (Year: 2019).*
Li et al., "Label-free colorimetric detection of trace cholesterol based on molecularly imprinted photonic hydrogels", 2011, J. Mater. Chem., 21, 19267 (Year: 2011).*

* cited by examiner (a)

(b)

SENSING DEVICE FOR DETECTING ANALYTE CONTAINING NON-METALLIC ELEMENT, AND METHOD THEREOF

CROSS-REFERENCE TO RELATED APPLICATIONS

The present application for patent claims the benefit of U.S. Provisional Patent Application No. 62/973,591 filed Oct. 15, 2019, the entire disclosures of which is incorporated herein by reference.

STATEMENT REGARDING FEDERALLY SPONSORED RESEARCH OR DEVELOPMENT

The invention was made with the US EPA Small Business Innovation Research (SBIR) support under Contract No. 68HERD19C0010. The government has certain rights in the invention.

NAMES OF PARTIES TO A JOINT RESEARCH AGREEMENT

Not applicable.

REFERENCE TO AN APPENDIX SUBMITTED ON COMPACT DISC

Not applicable.

FIELD OF THE INVENTION

The present invention generally relates to a sensing device comprising a working sensor for detecting an analyte containing a non-metallic element, and a method of using the device.

BACKGROUND OF THE INVENTION

Currently, there exists a need for sensors and sensing devices used for detecting or measuring analytes containing a non-metallic element. For example, compounds from a large family of perfluorinated chemicals (PFCs), such as perfluorooctane sulphonate (PFOS) and perfluorooctanoic acid (PFOA), have attracted worldwide attention in the scientific regulatory community and among the public due to their persistent, bio-accumulative, and toxic characteristics that can significantly deteriorate human health. PFOS and PFOA have found significant usage in many industrial and consumer applications that require high chemical stability and dirt-water-oil repellency, characteristics which are provided by the strong electro-negativity and small atomic size of fluorine molecules. They are also used for firefighting at airfields because of their inherent ability to create aqueous firefighting form foams (AFFFs) to extinguish fuel and hydrocarbon fires. Unfortunately, the chemical nature of fluorine makes the carbon-fluorine bond the strongest in nature, which makes these fluorinated compounds resistant to chemical or biochemical reactions and degradation processes. Due to increasing concerns over the long-term health effects of PFOS and Per- and Polyfluoroalkyl Substances (PFAS) on the human body, regulatory agencies have set limits for the concentrations of PFOS and PFAS in drinking water. In 2016, the United States Environmental Protection Agency (USEPA) established a lifetime health advisory (LHA) level of 70 parts per trillion (ppt) for individual or combined concentrations of PFOA and PFOS in drinking water. Recent studies indicate that exposure to PFOA and PFOS over certain levels may result in adverse health effects, including developmental defects in fetuses and breastfed infants, cancer, liver effects, immune effects, thyroid effects, and others. Hence, the development of trace detection and monitoring systems for PFOS and PFOA in water is highly necessary.

Currently, mass-spectrometry-based technologies are the main methods used to detect trace perfluorinated acids in various samples with sufficient sensitivity and selectivity. However, these methods require large and expensive equipment, have high operation costs, and sometimes suffer matrix interferences, making them unsuitable for routine analysis of PFOS and PFOA in the field.

Lab analysis for PFAS (EPA 537) is time-consuming and expensive, taking as long as 3 weeks and costing up to $450 per sample. Mobile labs can be rented for ~$500/week to cut down on analysis time. The detection of PFAS compounds in the field remains a big, problem to solve. People currently send all samples back to a lab, which is time-consuming and expensive and creates bottlenecks for fairly large projects.

Advantageously, the present invention provides a novel sensor and a sensing device that exhibit numerous technical merits. For example, the invention fieldable, fast (minutes vs two weeks for lab measurement), and much cheaper ($20 to $30 per sample vs $200 to $300 per sample for lab measurement) than the techniques currently on the market.

SUMMARY OF THE INVENTION

One aspect of the present invention provides a sensing device comprising a working sensor for detecting an analyte containing a non-metallic element. The working sensor comprises a sensing body including a 3D array of voids each having a void internal wall. At least a part of the voids are interconnected to each other and are configured to expose to the analyte, and admit the analyte into the at least a part of the voids. Void internal walls of the at least a part of the voids have cavities each having a cavity internal wall. Each of the cavities has a shape that is complementary to a shape of the analyte. The cavity internal wall is made from a material containing the non-metallic element.

Another aspect of the invention provides a method of measuring an analyte containing a non-metallic element using the aforementioned sensing device. The method includes (i) contacting a sample of the analyte with the working sensor, (ii) binding the analyte to the cavities and inducing or triggering a detectable variation of the optical property of the 3D array of voids, including a spectrum of light that is transmitted through, reflected from, and/or diffracted from the 3D array of voids, and (iii) correlating a degree of the detectable variation to an amount of the analytes bound to the cavities.

The above features and advantages and other features and advantages of the present invention are readily apparent from the following detailed description of the best modes for carrying out the invention when taken in connection with the accompanying drawings.

BRIEF DESCRIPTION OF THE SEVERAL VIEWS OF THE DRAWINGS

The present invention is illustrated by way of example, and not by way of limitation, in the figures of the accompanying drawings and in which like reference numerals refer to similar elements. All the figures are schematic and generally only show parts which are necessary in order to elucidate the invention. For simplicity and clarity of illustration, elements shown in the figures and discussed below have not necessarily been drawn to scale. Well-known structures and devices are shown in simplified form, omitted, or merely suggested, in order to avoid unnecessarily obscuring the present invention.

DETAILED DESCRIPTION OF THE PREFERRED EMBODIMENT

In the following description, for the purposes of explanation, numerous specific details are set forth in order to provide a thorough understanding of the present invention. It is apparent, however, to one skilled in the art that the present invention may be practiced without these specific details or with an equivalent arrangement.

Where a numerical range is disclosed herein, unless otherwise specified, such range is continuous, inclusive of both the minimum and maximum values of the range as well as every value between such minimum and maximum values. Still further, where a range refers to integers, only the integers from the minimum value to and including the maximum value of such range are included. In addition, where multiple ranges are provided to describe a feature or characteristic, such ranges can be combined.

It is also to be understood that the terminology used herein is for the purpose of describing particular embodiments only, and is not intended to limit the scope of the invention. For example, when an element is referred to as being "on", "connected to", or "coupled to" another element, it can be directly on, connected or coupled to the other element or intervening elements may be present. In contrast, when an element is referred to as being "directly on", "directly connected to", or "directly coupled to" another element, there are no intervening elements present.

Figure 1:
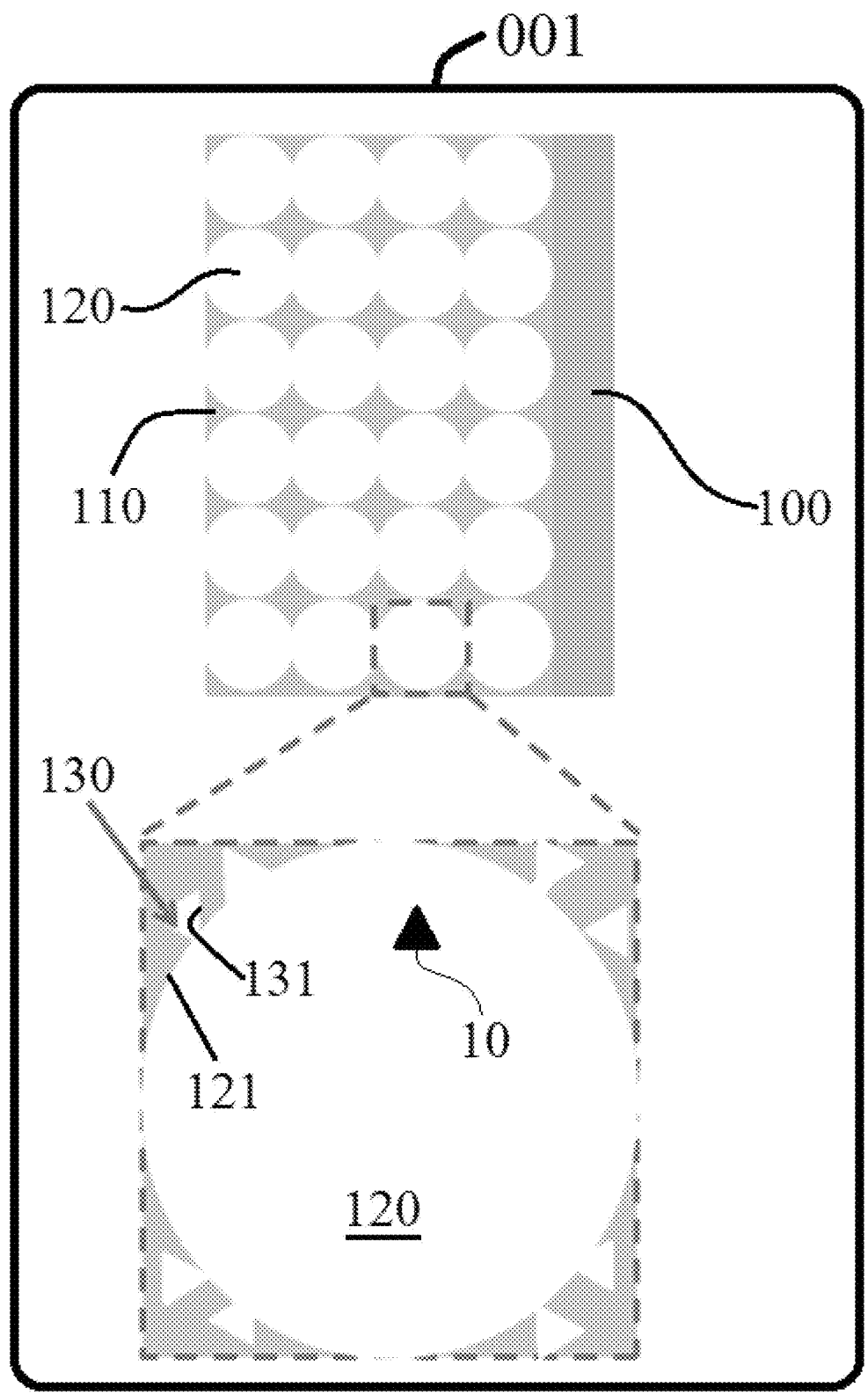
FIG. 1 schematically shows a sensing device comprising a working sensor in accordance with an exemplary embodiment of the present invention.

With reference to FIG. 1, various embodiments of the invention provide a sensing device 001 comprising a working sensor 100 for detecting an analyte 10 containing a non-metallic element. The sensor 100 comprises a sensing body 110 including a 3D array of voids 120 each having a void internal wall 121. At least a part of the voids 120 are interconnected to each other and are configured to expose to the analyte 10, and admit the analyte 10 into the at least a part of the voids 120. Void internal walls 121 of the at least a part of the voids 120 have cavities 130 each having a cavity internal wall 131. Each of the cavities 130 has a shape that is complementary to a shape of the analyte 10, like a lock-key interrelationship. The cavity internal wall 131 is made from a material that also contains the non-metallic element. In preferred embodiments, at least some of the non-metallic elements in the cavity internal wall material are directly exposed (i.e. not buried inside the material) to the cavity space, to facilitate the interaction or affinity between the non-metallic elements in the cavity internal wall material and the non-metallic elements in the analyte within the cavity.

Figure 2A:
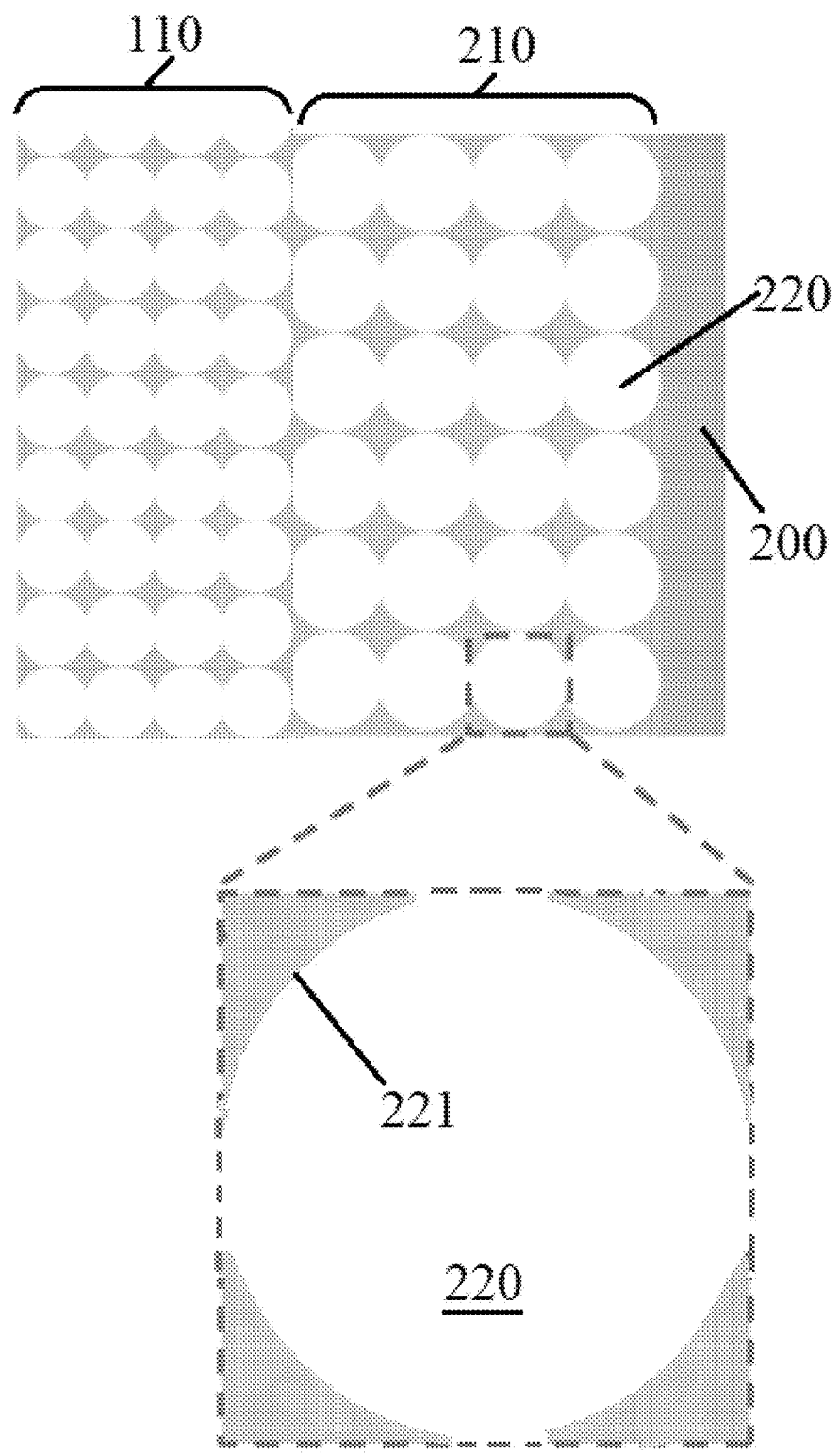
FIG. 2A illustrates a sensing device comprising a working sensor and a reference sensor in accordance with an exemplary embodiment of the present invention.

With reference to FIG. 2A, various embodiments of the invention provide a sensing device 001 that further includes a reference sensor 200. Sensor 200 is the same as the working sensor 100 except that (1) the reference sensor 200 does not include the cavities 130 as those in the working sensor 100, and (2) voids 220's size of the reference sensor 200 is different from (bigger than or smaller than) voids 120's size of the working sensor 100.

In various exemplary embodiments, the non-metallic element may be selected from F, Cl, Br, I, O, S, Se, Te, N, P, As, Sb, B, C, H, or any combination thereof, among which F, Cl, Br, I, O, S, Se, Te, N, P, As, and Sb are preferred due to strong intermolecular interaction or affinity between electronegative elements e.g. F—F, Cl—Cl, Br—Br, I—I, O—O, S—S, Se—Se, Te—Te, N—N, P—P, As—As, and Sb—Sb.

In various exemplary embodiments, the sensing body, the void internal walls, and the cavity internal walls may be made from same or different material. In preferred embodiments, the sensing body, the void internal walls, and the cavity internal walls are all made from a same material containing the non-metallic element. For example, such same material may comprise a polymer prepared from photo polymerization and/or thermal polymerization using monomers containing the non-metallic element. In a specific embodiment, such same material is prepared from a pre-polymerization composition comprising the monomers containing the non-metallic element, the analyte containing the non-metallic element, and an optional cross-linking agent. For example, the pre-polymerization composition may include template/analyte molecule PFOA; functional monomers including 2-(trifluoromethyl) acrylic acid (TFMAA), 2-(difluoromethyl) acrylic acid (DFMAA), and/or 2-(monofluoromethyl) acrylic acid (MFMAA), and cross-linking agent EGDMA that utilizes an interaction between the non-metallic elements such as fluorine-fluorine interactions, electrostatic attraction, and associated weak interactions. In some embodiments, the pre-polymerization composition further comprises monomers that do not contain the non-metallic element such as acrylic acid (AA), methyl acrylic acid (MAA), and any mixture thereof.

In various exemplary embodiments, the array of voids is a 3D array of voids formed by removing a colloidal crystal from a solid body into which the colloidal crystal is incorporated and integrated. For example, the colloidal crystal may include silica nanoparticles, polystyrene nanoparticles, or any combination thereof. The size (diameter) of the voids may be in the range of from 180 nm to 400 nm.

In various exemplary embodiments, the 3D array of voids may be formed by stacking a number of 2D array of voids, and a height of the stack of 2D array of voids, or a thickness of the 3D array of voids, may be approximately 2-10 µm. For example, the 3D array of voids may be formed by stacking 5-20 (e.g. 10) layers of 2D array of voids. The 2D array of voids (e.g. measured from the top layer) may have a uniform area of 0.01-4 cm$^2$ such as larger than 2×2 mm$^2$ and up to 2×2 cm$^2$.

In various exemplary embodiments, the sensing body is deposited on a polymer plate such as a polymethyl methacrylate (PMMA) plate.

In various exemplary embodiments, a binding of the analytes to the cavities induces or triggers a detectable variation of the optical property of the 3D array of voids, including the spectrum of light that is transmitted through, reflected from, and/or diffracted from the 3D array of voids, and a degree of the detectable variation is correlated with the amount of the analytes bound to the cavities. The sensing device of the invention may include a light source such as a laser emitting light e.g. a light beam that irradiate upon the 3D array of voids (as incident light). A spectrometer may be then used to measure the spectrum of light that is transmitted through, reflected from, and/or diffracted from the 3D array of voids. A computer may be used to record and analyze the obtained spectrum or spectra.

Figure 2B:
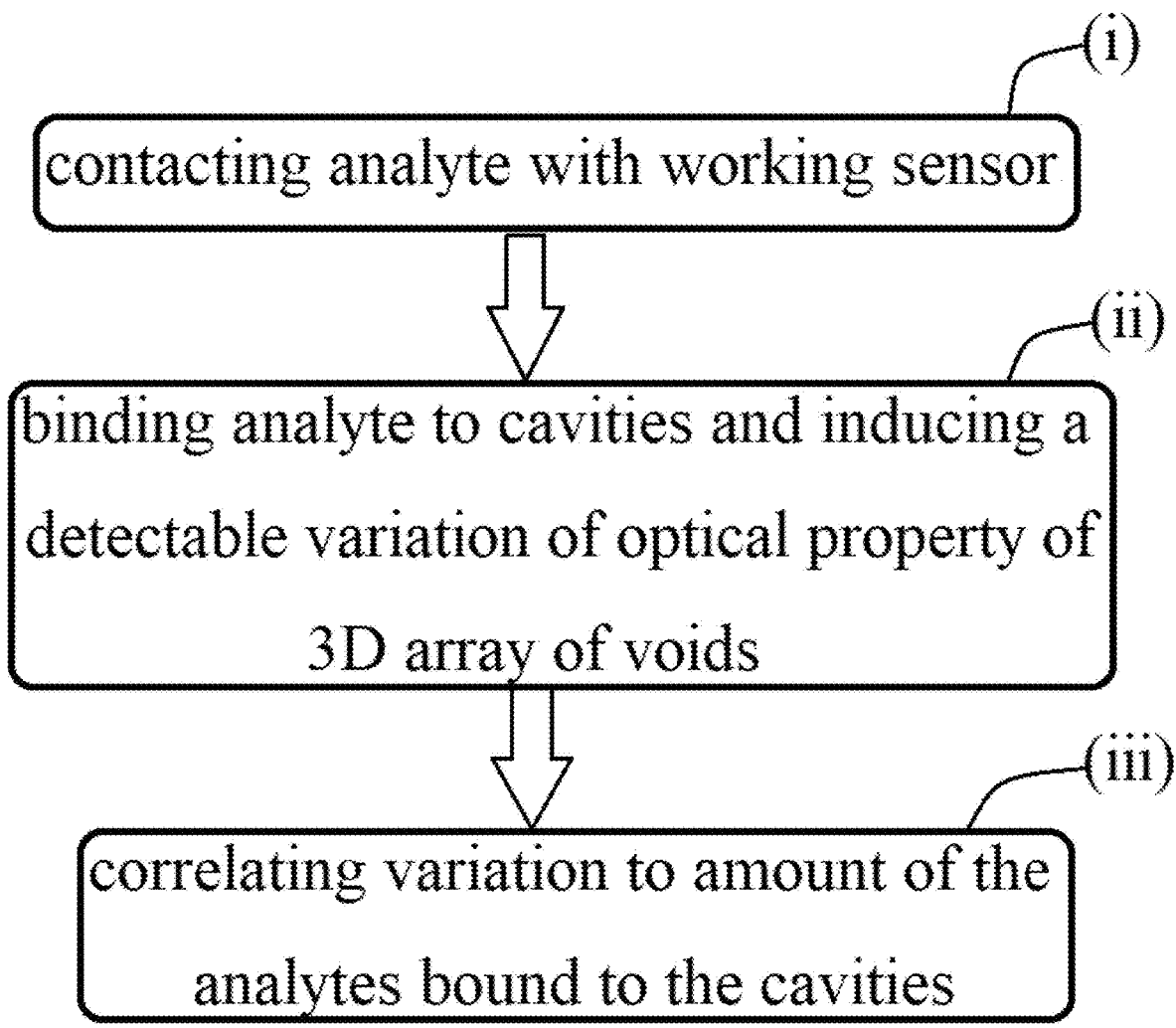
FIG. 2B is a flow chart of a method for measuring an analyte containing a non-metallic element in accordance with an exemplary embodiment of the present invention.

In various exemplary embodiments, the present invention provides a method of measuring an analyte containing a non-metallic element using the sensing device as described above. As shown in FIG. 2B, the method includes (i) contacting a sample of the analyte with the working sensor, (ii) binding the analyte to the cavities and inducing or triggering a detectable variation of the optical property of the 3D array of voids, including a spectrum of light that is transmitted through, reflected from, and/or diffracted from the 3D array of voids, and (iii) correlating a degree of the detectable variation to an amount of the analytes bound to the cavities.

For example, the analyte may contain F, C, and/or H. In specific embodiments, the analyte is selected from fluorinated chemicals such as perfluorinated chemicals (PFCs), e.g. perfluoroalkyl substance, for example, perfluorooctane sulphonate (PFOS) and perfluorooctanoic acid (PFOA), an herbicide such as atrazine, and PFAS (EPA 537).

In representative and still exemplary embodiments, the present invention provides a platform sensing technology for field trace detection of analytes 10 such as PFOA and PFOS in groundwater. A representative embodiment of the working sensor 100 is a photonic crystal-based polymer sensing chip with cavities 130 such as molecularly imprinted (MIP) binding sites, which can selectively bind to PFOA and PFOS molecules in water and produce specific optical signals that are read using a portable UV-Ms spectrometer and correlated to the concentration of PFOA and PFOS in water. The "molecularly-imprinted photonic crystal" can show the colors of rainbow through nano and molecular engineering. Such a working sensor 100 exhibits the following advanced attributes: high sensitivity, high specificity, fast detection, ease of operation, low power consumption, zero chemical release, and low operation cost. Moreover, direct use of the sample water eliminates any uncertainty associated with measurement technique or complicated separation processes. For example, such a MIP sensor 100 may be used for detecting, herbicide atrazine in water.

Figure 3:
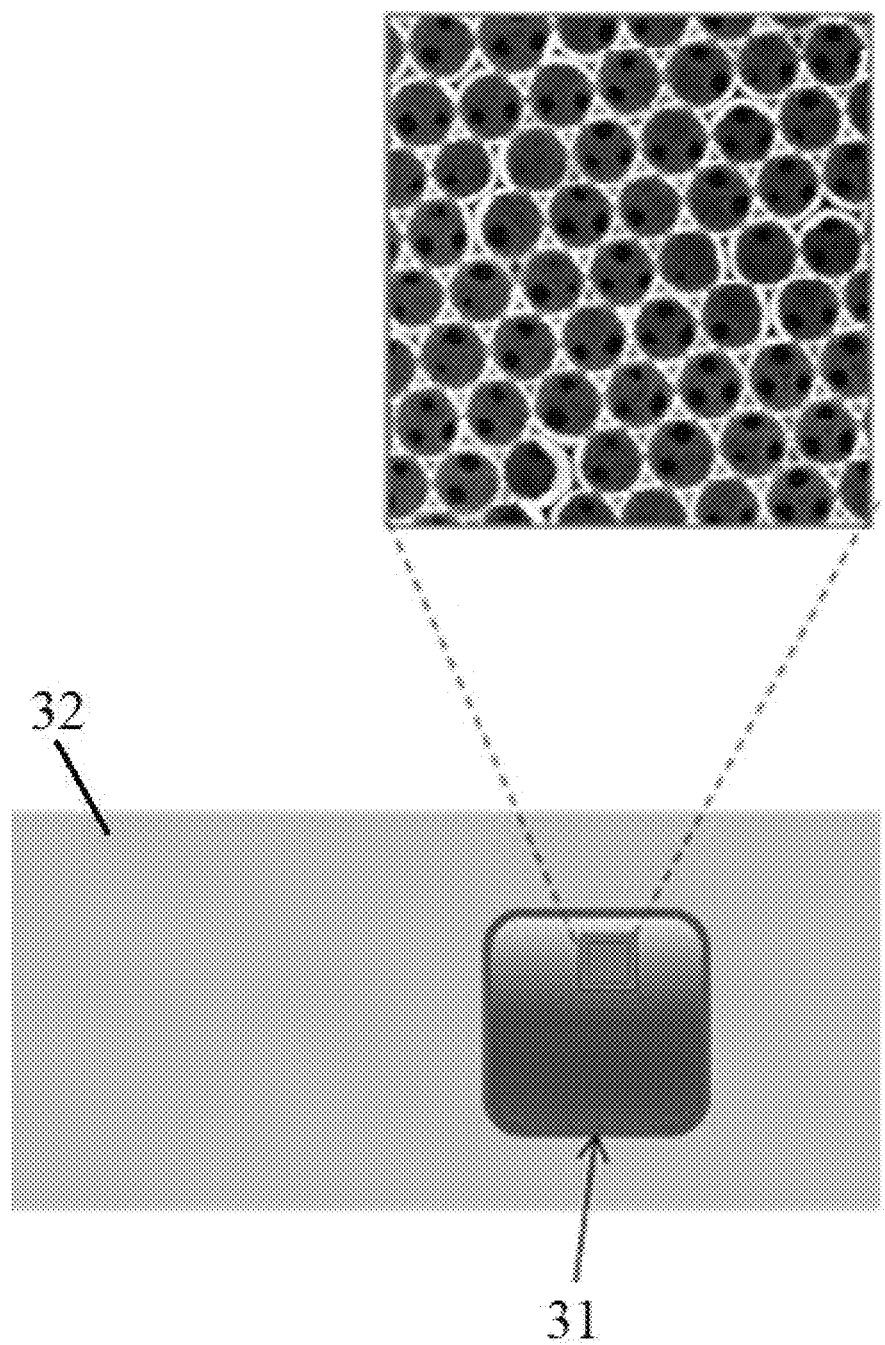
FIG. 3 illustrates a photonic crystal sensing chip in accordance with an exemplary embodiment of the present invention.

As a representative and still exemplary embodiment of the 3D array of voids 120, a photonic crystal sensing chip 31 consists of a 3D-ordered interconnected macroporous structure. For ease of use, the chip 31 may be assembled onto a clear microscope slide support 32, as shown in FIG. 3. In the photonic crystal structure, numerous nanocavities (as an embodiment of cavities 130 in FIG. 1) derived from removed analytes 10 such as template molecules (PFOA/PFOS in this embodiment) may be distributed in the thin walls (as an embodiment of cavity internal wall 131 in FIG. 1) of the ordered macro-pores (inverse polymer opal). During detection, these nanocavities will recognize the template molecules with high specificity and induce a change in the refractive index of the ordered structure. The color of the sensor will change via Bragg diffraction, which can be detected using a portable UV-Vis spectrometer (a reader). The color change (i.e. absorption peak shift) of the sensor will be correlated with the concentration of template molecule in water. Based on this embodiment, an autonomous PFOA and PFOS monitoring system can be developed, including water sampling, measurement, data processing, and reporting.

With no intention of being bound by any particular theory, it is believed that once molecular recognition occurs, the trapped analyte molecules (i.e. binding of analyte 10 to cavity 130) will cause either swelling or shrinkage of the prepared hydrogel, leading to refractive index change. The refractive index change of the sensing element will induce its diffraction peak shift, which can be detected optically and correlated with the concentration change of PFOA in water.

The diffraction peak, $\lambda_{max}$, for the porous hydrogel is determined by the Bragg equation (1):

$$\lambda_{max} = 1.633\left(\frac{d}{m}\right)\left(\frac{D}{D_0}\right)(n_a^2 - \sin\theta^2)^{1/2} \quad (1)$$

where d is the sphere diameter of the silica colloidal particle (which is also one way to define voids 120's size of the working sensor 100), in is the order of Bragg diffraction, ($D/D_0$) is the degree of swelling of the gel (D and $D_0$ denote the diameters of the gel in the equilibrium state at a certain condition and in the reference state, respectively), $n_a$ is the average refractive index of the porous gel at a certain condition, and θ is the angle of incidence. According to this equation, if the molecular recognition process could cause swelling or shrinkage of the prepared hydrogel, then the readable optical signal is detectable.

Figure 4:
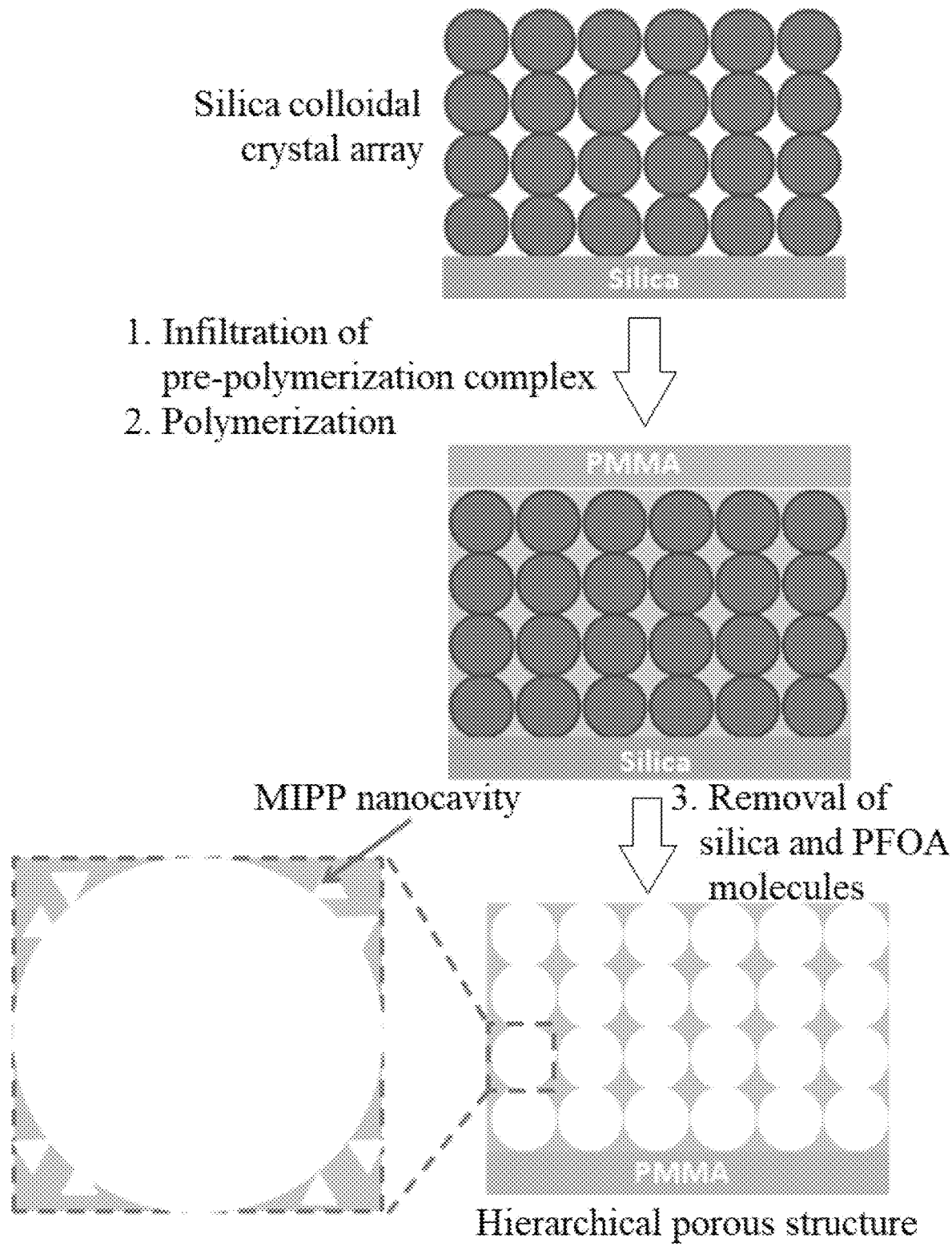
FIG. 4 demonstrates the fabrication procedure for a hierarchical porous sensor chip sensing chip in accordance with an exemplary embodiment of the present invention.

In a representative and still exemplary embodiment, the fabrication procedure for a hierarchical porous sensor chip sensing chip is schematically shown in FIG. 4. The procedure starts with the preparation of a colloidal crystal template or array, followed by the infiltration and polymerization of the pre-ordered complex of PFOA with functional monomers (pre-polymerization complex) in the inter-spacers of the colloidal crystal, and then the removal of the used templates (colloid particles and PFOA/PFOS molecules). The feasibility of MIP photonic crystal-based sensing has been demonstrated by Zhen Wu et al, "Label-free colorimetric detection of trace atrazine in aqueous solution by using molecularly imprinted photonic polymers" Chemistry—A European Journal, v 14, n 36, p 11358-11368, which is incorporated herein by reference. In their approach, colloidal crystal templates used to form inverse polymer opals were created using a solvent evaporation colloidal crystal growth method, which normally requires several days. In contrast, the present invention provides a scalable two-phase assembly and transfer technique to fabricate colloidal crystal templates, which significantly reduces the preparation time to less than one hour.

Referring to FIG. 4, the procedure for sensing chip fabrication includes the following steps. (1) Preparation of colloidal crystal arrays: Silica colloidal crystal arrays are prepared using a two-phase self-assembly and transfer process to form highly ordered 3D macroporous structures. The size of monodispersed silica particles may range from 180 nm to 400 nm. Self-assembled monolayers of silica particles are stacked onto a glass support to form a multi-layer photonic crystal film with a thickness of approximately 3-5 µm. (2) Infiltration and polymerization of pre-polymerization complex: In order to fabricate the PFOA-imprinted polymer hydrogel, the template molecule (PFOA), functional monomers (TFMAA), and cross-linking agent (EGDMA) are first mixed to generate a pre-polymerization cluster that utilizes fluorine-fluorine interactions, electrostatic attraction, and associated weak interactions. The mixture is then filled into the void spaces of the colloidal crystal array via capillary force by using a sandwich structure of PMMA/nanoparticle array/silica. Upon polymerization, the structure is frozen in a 3D network of polymers. (3) Removal of template particles and molecules: The removal of silica particles and the embedded PFOA molecules from the imprinted polymer matrix yields highly-ordered 3D and interconnected macroporous arrays with specific nanocavities that interact with PFOA molecules through non-covalent interactions

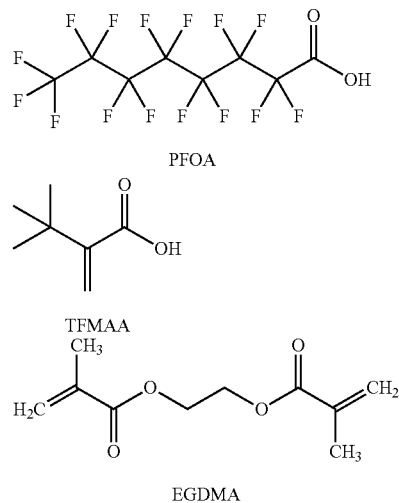

In preferred embodiments, the invention provides (1) a two-phase assembly method to fabricate colloidal crystal templates with a uniform area larger than 1 cm²; (2) Preparation of inverse polymer opal sensors with specific binding sites for PFOA molecules using a fluorous monomer and cross-linker; (3) Fabrication of molecularly imprinted photonic crystal sensors on PIA support with a uniform area larger than 1 cm²; and (4) a demonstration of a reproducible calibration curve for a range of concentrations from 0 or 0.1 to 1000 ppt of PFOA in water. Specifically, silica nanoparticle colloidal crystal templates have been fabricated using a two-phase interface assembly method. A fabrication process for the molecularly imprinted sensor has been developed. A detection limit of 10 ppt has been achieved for trace detection of PFOA in a mixed solvent of water/methanol in a lab setting.

Figure 5:
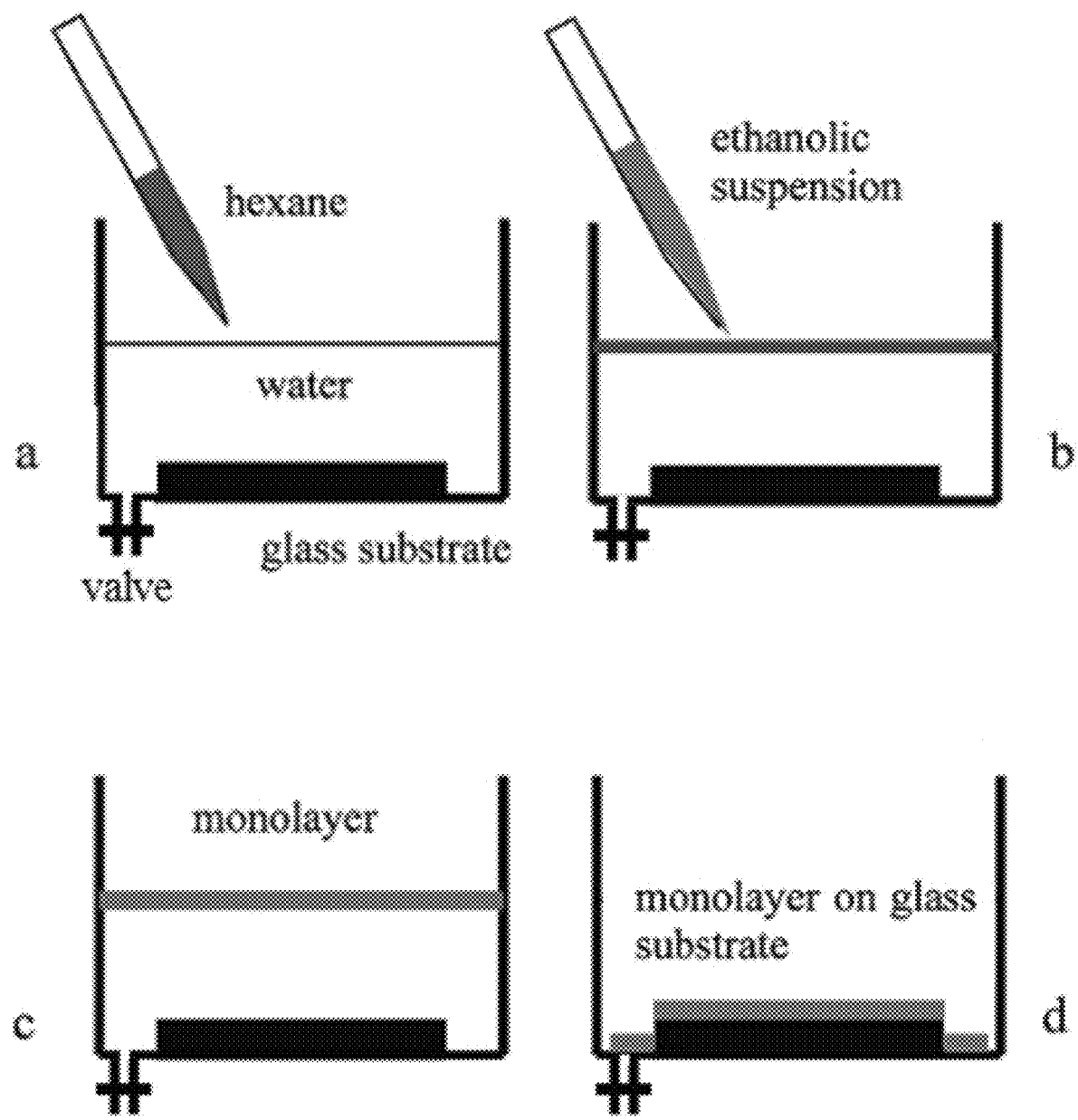
FIG. 5 depicts a colloid crystal template prepared using water-hexane interfacial assembly in accordance with an exemplary embodiment of the present invention.

In specific embodiments, the colloid crystal template was prepared using water-hexane interfacial assembly. As shown in FIG. 5, multi-layer colloid crystal templates were prepared on glass supports using a water/hexane interfacial assembly and transfer method. The process was started by positioning a pre-cleaned silica substrate on the bottom of a Petri dish. Then a suitable amount of water was poured into the Petri dish to immerse the substrate, followed by adding a few drops of hexane onto the water surface to form a thin organic solvent layer. A monolayer of silica colloidal nanoparticles was prepared by spreading the ethanol suspension (ca. 1% w/w) of silica nanoparticles onto the interface between the water and the thin layer of hexane in the Petri dish until the water surface was totally covered with a bead monolayer. Then the monolayer was lowered onto the substrate by decreasing the water level and allowing the water to flow out of the dish through a valve on the bottom. Multi-layer colloid crystal templates were fabricated by repeating this process until the desired number of layers was reached. Two kinds of silica nanoparticles with particle sizes of 180 nm and 300 nm were used to make colloid crystal templates with up to 10 layers. Two different glass substrates were used as support, including a circular disc of 18 mm in diameter and 0.17 mm in thickness and a square of 18 mm×18 mm with a thickness of 0.17 mm. Steps (a) and (b)

in FIG. 5 are spreading beads from ethanol dispersion on the water-hexane interface; step (c) is the formation of the bead monolayer; and step (d) is transfer of the bead monolayer onto glass substrate.

Figure 6:
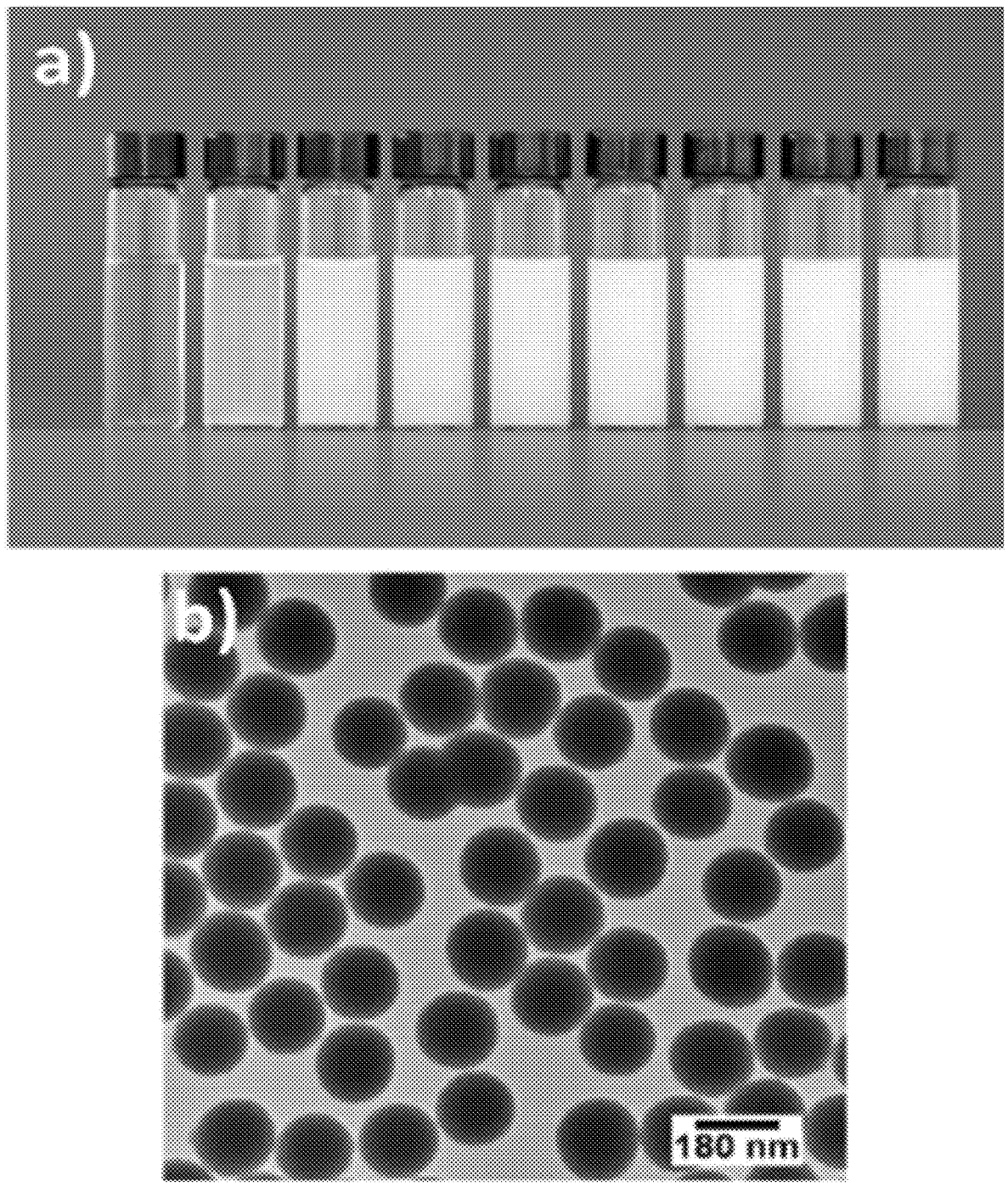
FIG. 6 shows images and size distribution of silica nanoparticle colloids in accordance with an exemplary embodiment of the present invention.
Figure 6:
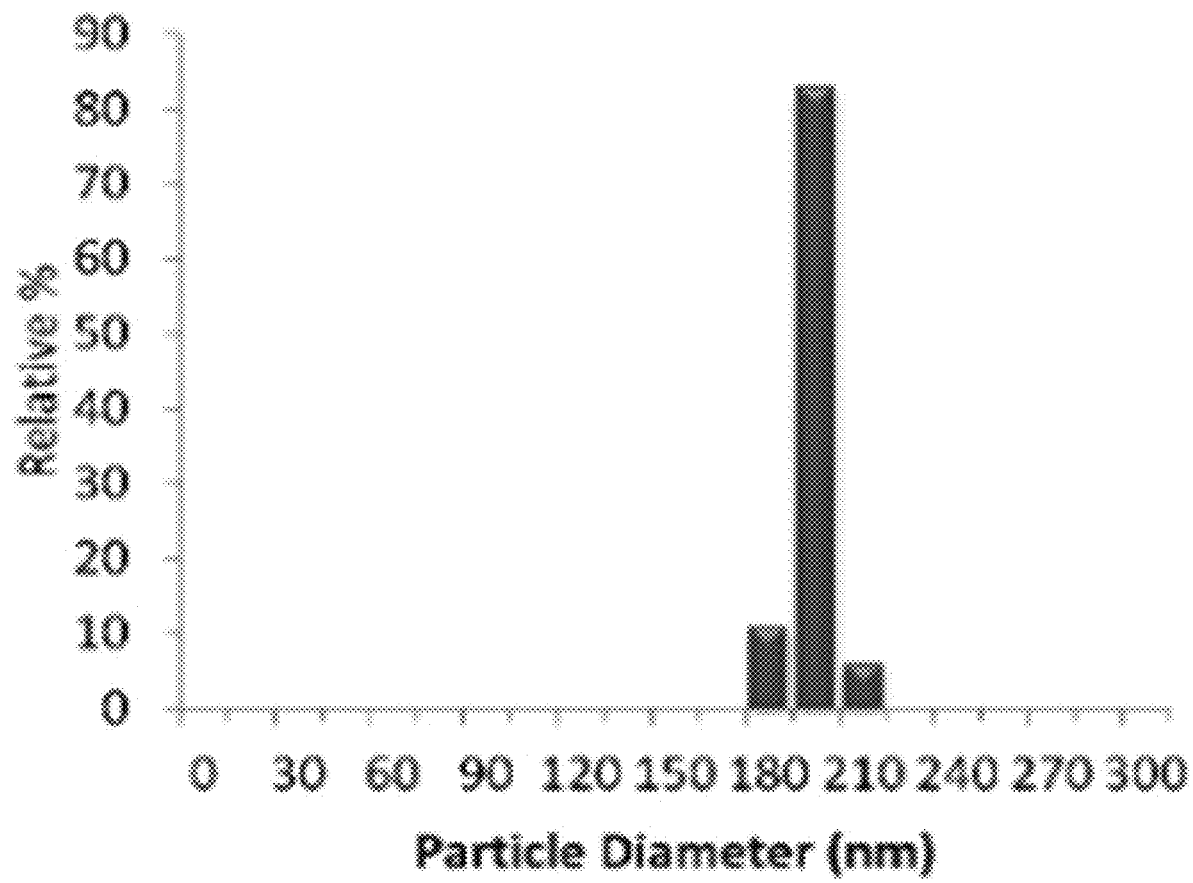

With reference to FIG. 6, silica nanoparticle colloids with different particle size in panel a) were purchased from NanoComposix (San Diego, Calif.) in colloid form Nano-Composix's silica nanospheres are monodisperse with diameters 20 nm and up, and are available with both bare and amine-terminated surfaces. Panels b) and c) show that ethanol-dispersed monodisperse silica nanoparticles of 180 nm and 300 nm were used. Panel b) shows a TEM image of the 180 nm silica particles, and Panel c) shows size distribution of particle obtained from multiple TEM images.

Figure 7:
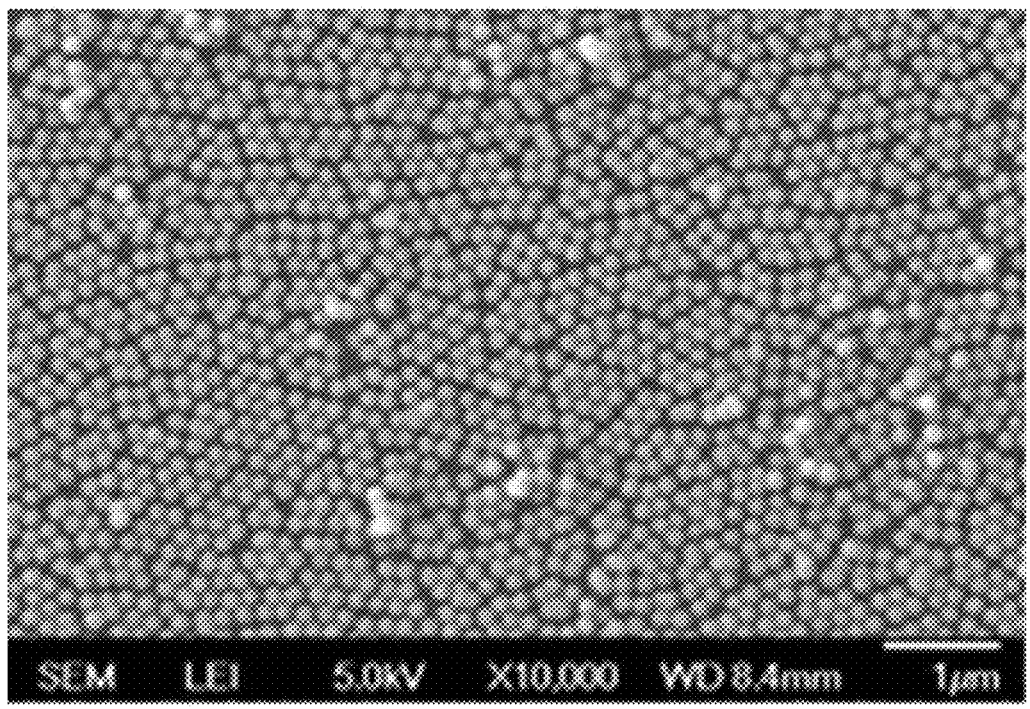
FIG. 7 shows SEM surface morphologies of 1-layer and 10-layer samples in accordance with an exemplary embodiment of the present invention.
Figure 7:
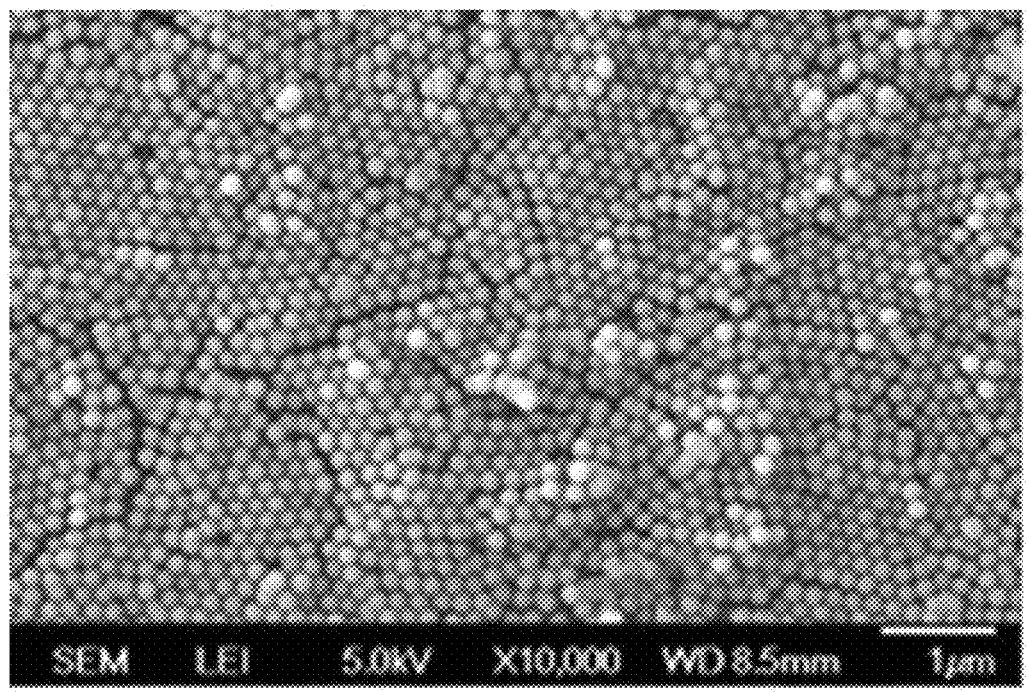

Multi-layer colloid crystal templates of 180 nm silica nanoparticles were fabricated by repeating the monolayer deposition process. The samples were annealed at 70° C. for 10 minutes after the deposition process to evaporate trapped water, hexane or ethanol from the template. It was found that this annealing process increases the adhesion between the particles and the glass substrate. FIG. 7 shows SEM surface morphologies of a 1-layer sample in panel (a) and 10-layer sample in panel (b) under the same magnification. It can be seen from this figure that a certain degree of order is retained in the 10-layer sample with a sufficient domain size.

Figure 8:
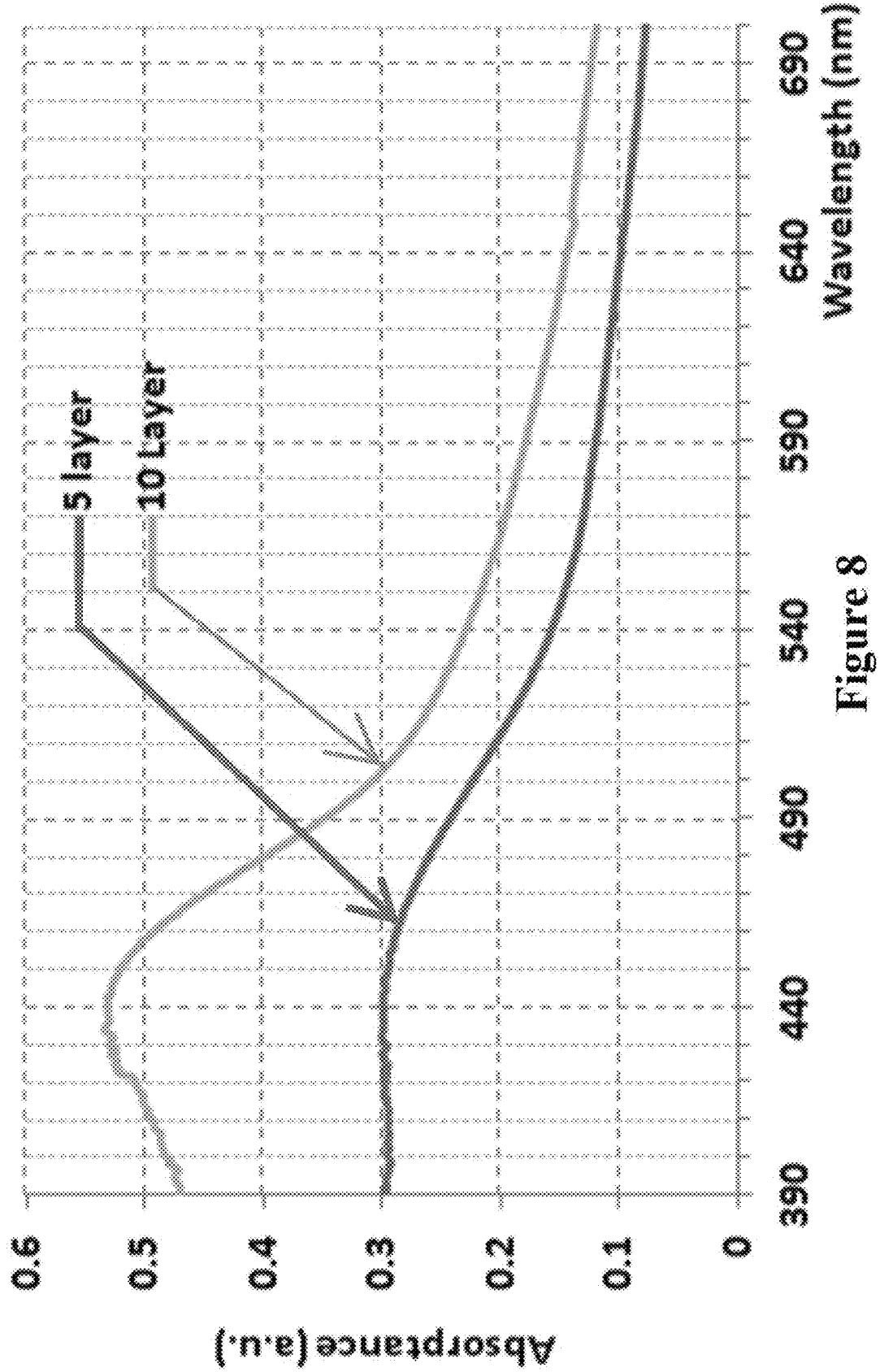
FIG. 8 shows the UV-Vis absorption spectra of a 5-layer and a 10-layer silica colloid crystal template with a particle size of 180 nm in accordance with an exemplary embodiment of the present invention.

The UV-Vis absorption spectra of a 5-layer and a 10-layer colloid crystal template were measured using a UV-Vis spectrometer. FIG. 8 shows the UV-Vis absorption spectra of a 5-layer and a 10-layer silica colloid crystal template with a particle size of 180 nm. As can be seen from the figure, there is no obvious absorption peak on the spectrum of the 5-layer sample (red curve). For the 10-layer sample, an absorption peak can be clearly seen on the spectrum (green curve). The absorption peak is believed to be caused by optical interference between the ordered nanoparticle layers. Optical interference is stronger in the 10-layer sample than in the 5-layer sample, which is why the absorption peak is more obvious in the 10-layer sample.

Figure 9:
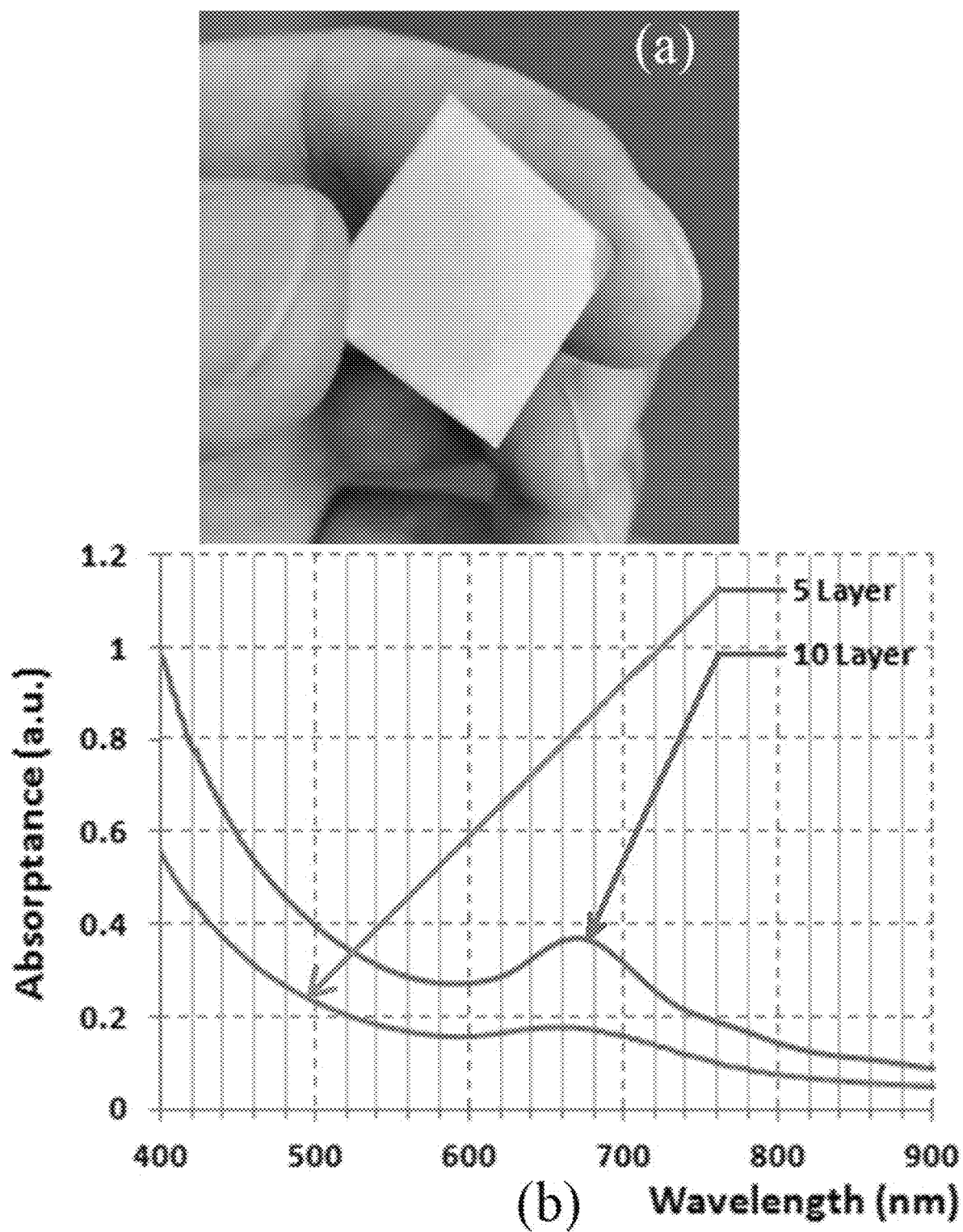
FIG. 9 shows vis-NIR spectra of a colloid crystal sample measured after assembly of 5 layers and 10 layers in accordance with an exemplary embodiment of the present invention.

Colloid crystal templates were also fabricated using 300 nm silica nanoparticles using a procedure similar to the one described above for 180 nm silica nanoparticles. FIG. 9 Panel (a) shows a 10-layer colloid crystal sample of 300 nm silica nanoparticles on 18 mm×18 mm glass substrate, and FIG. 9 Panel (b) shows vis-NIR spectra of the colloid crystal sample measured after assembly of 5 layers and 10 layers. A typical 10-layer colloid crystal sample is shown in FIG. 9 Panel (a) with vis-NIR spectra of this sample measured after assembly of 5 layers and 10 layers shown in FIG. 9 Panel (b). As can be seen from FIG. 9 Panel (b), the 300 nm sample possesses a strong absorption peak at 679 nm, which may be due to strong reflection from the ordered layers. This reflection in the red region of the solar spectrum results in the reddish appearance of the sample under white illumination (as shown in FIG. 9 Panel (a)). Comparison of spectra of the 180 nm and 300 nm samples indicates that increasing particle size from 180 nm to 300 nm causes a red shift of absorption peak from 438 nm to 668 nm.

Figure 10:
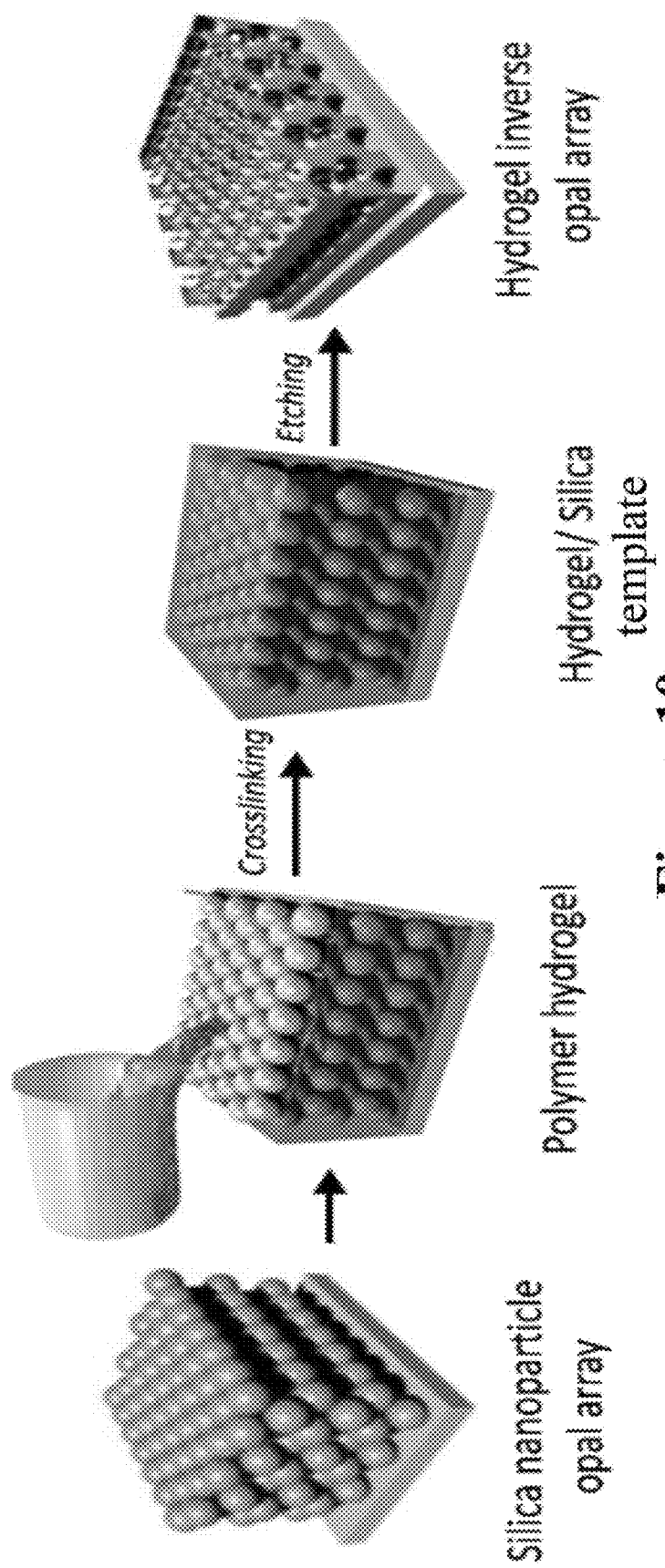
FIG. 10 illustrates a fabrication process for PFOA-imprinted inverse polymer opal structure in accordance with an exemplary embodiment of the present invention.

The fabrication process for the PFOA-imprinted inverse polymer opal structure was provided in an exemplary embodiment. PFOA-imprinted photonic polymer hydrogels were fabricated over the colloid crystal templates as shown in FIG. 10. Monomer solutions were poured over the opal structured 3D ordered array in order to obtain inverse opal replicas of a self-assembled colloidal crystal template via a noncovalent, self-assembly approach. The template molecule (PFOA), monomer (TFMAA), and cross-linking agent ethylene glycol dimethacrylate (EGDMA) were first mixed to generate a pre-polymerization cluster that utilizes fluorine-fluorine interactions, electrostatic attraction, and associated weak interactions.

Figure 11:
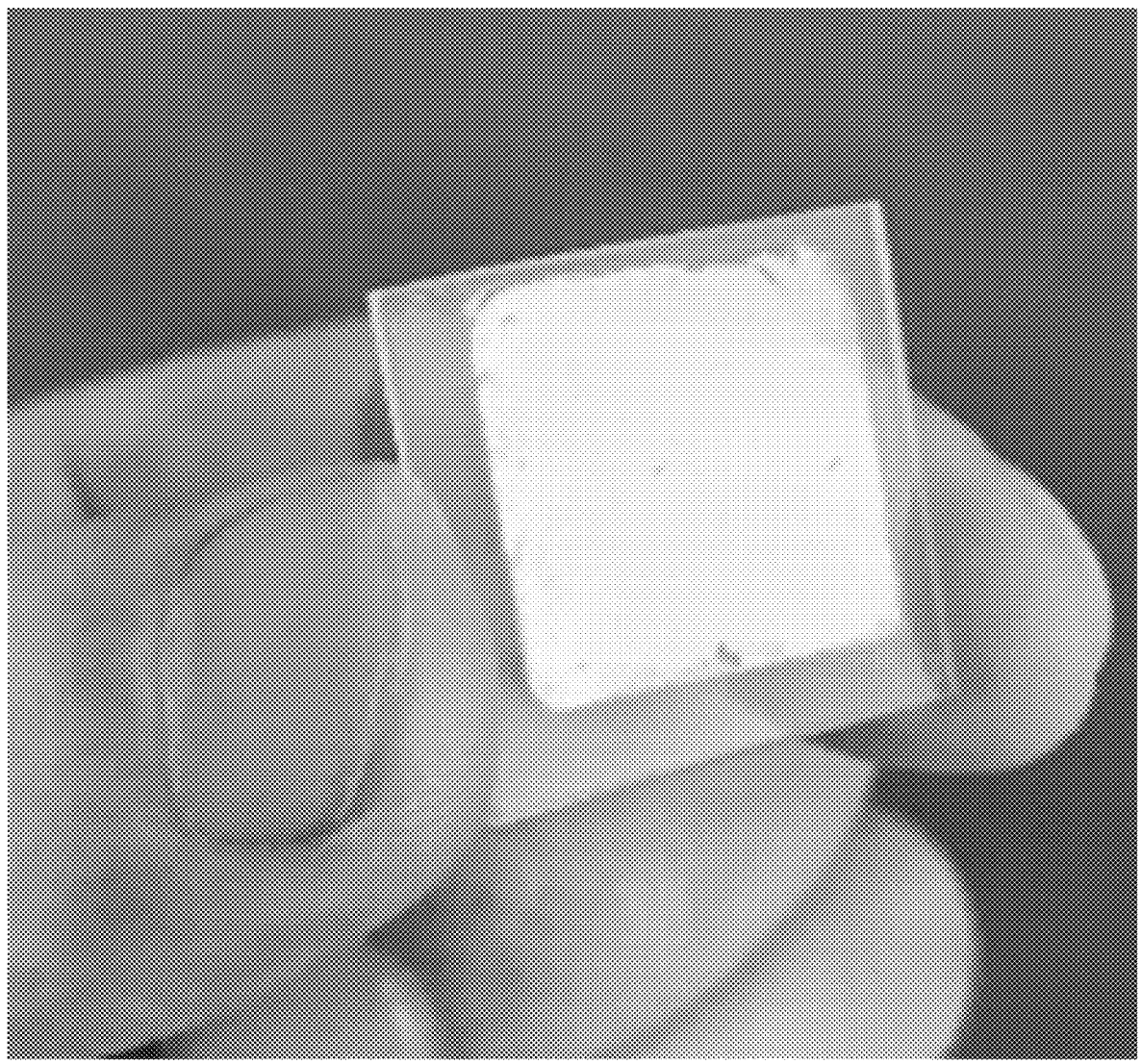
FIG. 11 shows a fabricated inverse opal sensor from a colloid crystal template of 300 nm nanoparticles in accordance with an exemplary embodiment of the present invention.

In a typical sensor preparation, PFOA, TFMAA and EGDMA were mixed in methanol at a molar ratio of 1:2:2 and left overnight to allow sufficient complexation Due to hydrogen bonding and fluorine-fluorine interaction, good dispersion of the analyte molecules in the matrix was achieved. Then, 3 wt % of AIBN was added as a radical initiator to initiate free radical polymerizations and the mixture was degassed with nitrogen for 10 min. A suitable amount of the well-dispersed monomer solution was poured over a colloid crystal template, which was then covered with a PMMA plate to form a sandwich structure. Once the colloidal crystal layer in the formed sandwich structure became transparent, a successful infiltration process was completed After the removal of excess precursors, photopolymerization was carried out under UV light at 365 nm for 2 h. The sandwich structure was then immersed in 20 wt % hydrofluoric acid for 2 hrs to fully etch the glass substrate and silica nanoparticles. The formed inverse opal polymer layer remained on the PMMA plate. The embedded PFOA molecules were removed by incubating the polymer film in an acetic acid/methanol mixture for 30 min, followed by drying in an ambient environment. A fabricated inverse opal sensor from a colloid crystal template of 300 nm nanoparticles is shown in FIG. 11. For control experiments, non-imprinted photonic hydrogel (NIPP) films may be prepared by using the same procedure and conditions, only without the addition of PFOA molecules FIG. 11 shows a fabricated inverse opal sensor from a colloid crystal template of 300 nm nanoparticles.

Figure 12:
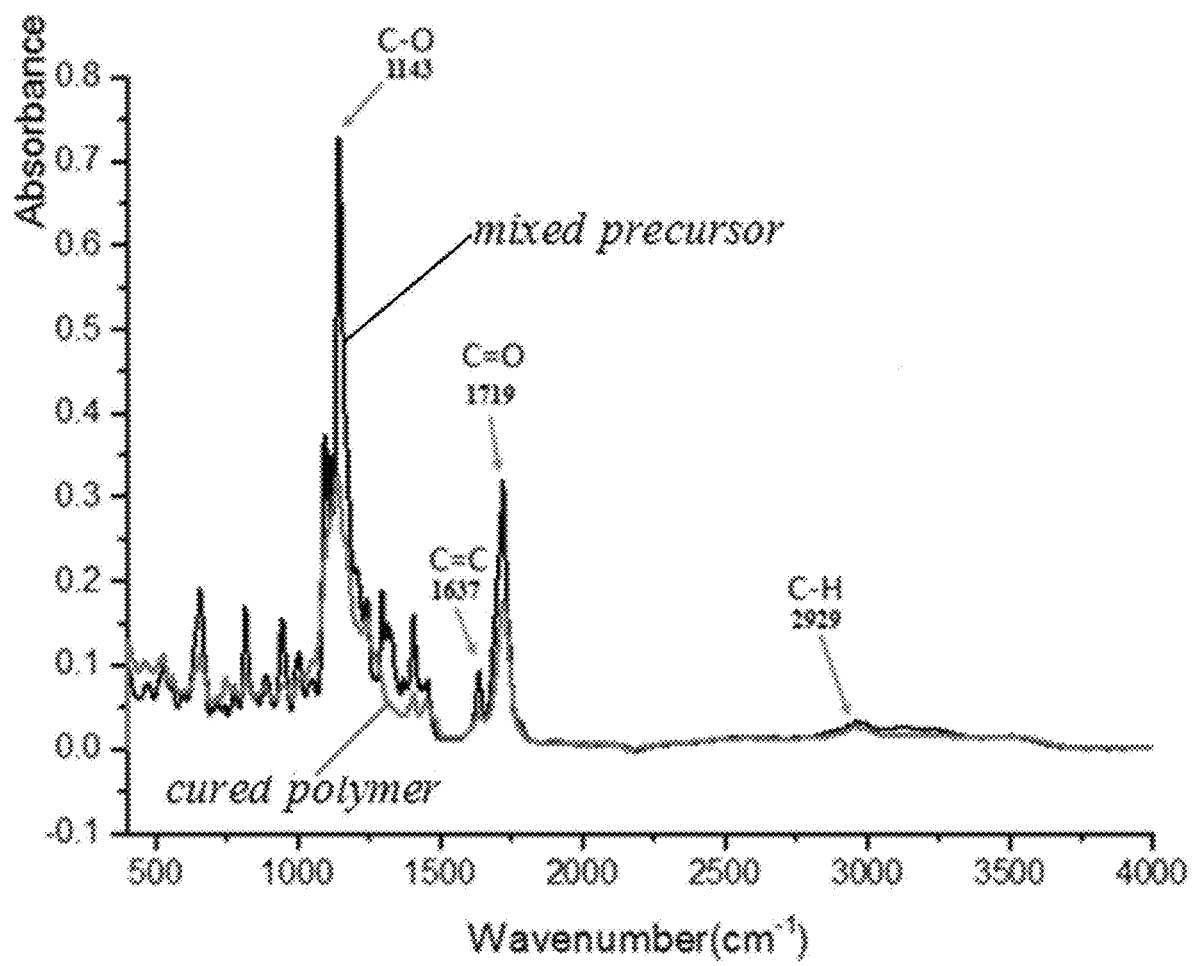
FIG. 12 shows FTIR spectra of a UV-cured polymer (red) and a mixed precursor solution (black) in accordance with an exemplary embodiment of the present invention.

UV cross-linking of the mixed precursors was investigated using FTIR spectroscopy. After 2 hours of UV polymerization, the sample was measured using a FTIR to identify spectral peaks of molecular groups in the polymer sample. FTIR spectra of a UV-cured polymer (red) and the mixed precursor solution (black) are shown in FIG. 12. From these spectra, it can be clearly seen that the vibration peaks at 1637 cm$^{-1}$ of the C=C groups were significantly reduced in the polymer sample compared with that in the spectrum from the precursor solution. This means that the UV curing conditions can polymerize the monomer solution into a polymer FIG. 12 shows the FTIR spectra of a UV-cured polymer (red) and the mixed precursor solution (black), with C=C vibration peak showing at 1637 cm$^{-1}$.

Figure 13:
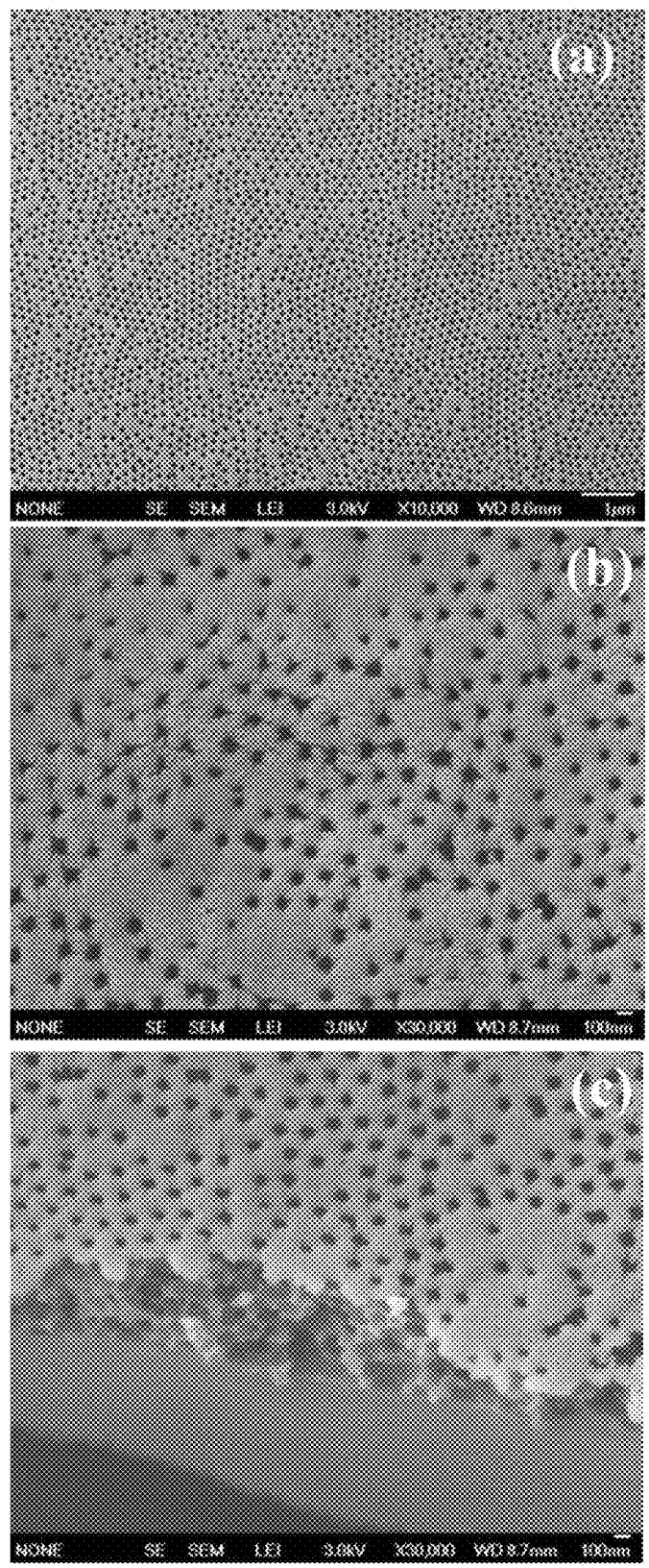
FIG. 13 shows surface morphologies of the fabricated reverse opal polymer structures at different magnifications in accordance with an exemplary embodiment of the present invention.

The surface morphologies of the fabricated reverse opal polymer structures were observed using. SEM. FIG. 13 shows the surface morphologies at different magnifications. As can be seen from these images, the glass support and silica nanoparticles have been completely etched away. FIG. 13 includes surface morphologies of an inverse opal polymer structure at different magnifications (panels (a) and (b)) and at the edge of the structure (panel (c)).

Figure 14:
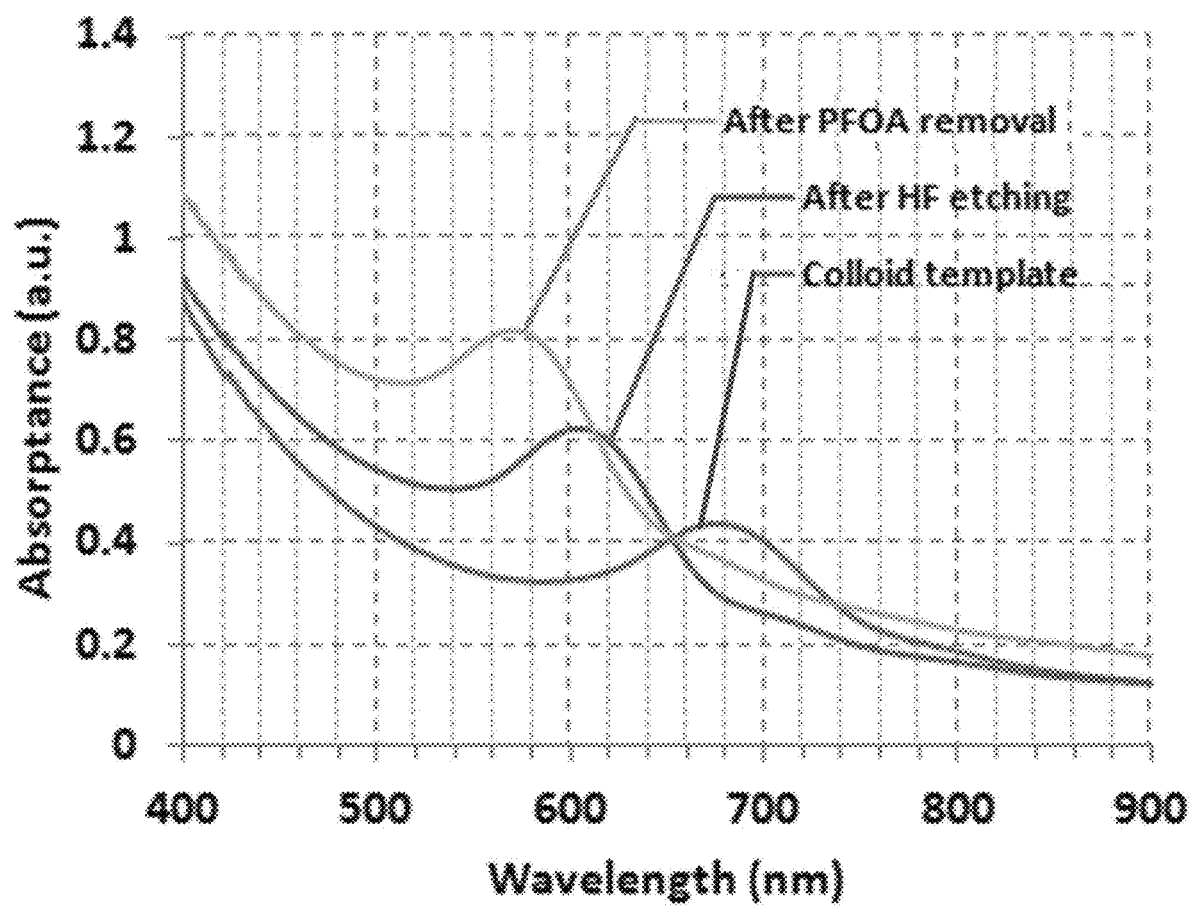
FIG. 14 shows vis-NIR spectra of the fabricated inverse opal sensor after HF etching (red) and after PFOA removal (green) in accordance with an exemplary embodiment of the present invention.

The vis-NIR spectra of the fabricated inverse opal sensor after HF etching (red) and after PFOA removal (green) are shown in FIG. 14, together with a vis-NIR spectrum of the template for comparison (blue). After UV polymerization of the mixed precursors, the fluoro-containing polymer has a lower refractive index, leading to blue shift of the absorption peak (from 679 nm to 604 nm) for the etched opal structure compared with that of the template. After PFOA removal, there is further blue-shifting of the absorption peak to 569 nm, which is caused by the refractive index reduction from PFOA removal FIG. 14 shows Vis-NIR spectra of the inverse opal sensor after HF etching (red) and after PFOA removal (green), a vis-NIR spectrum of the template is given for comparison (blue).

Figure 15A:
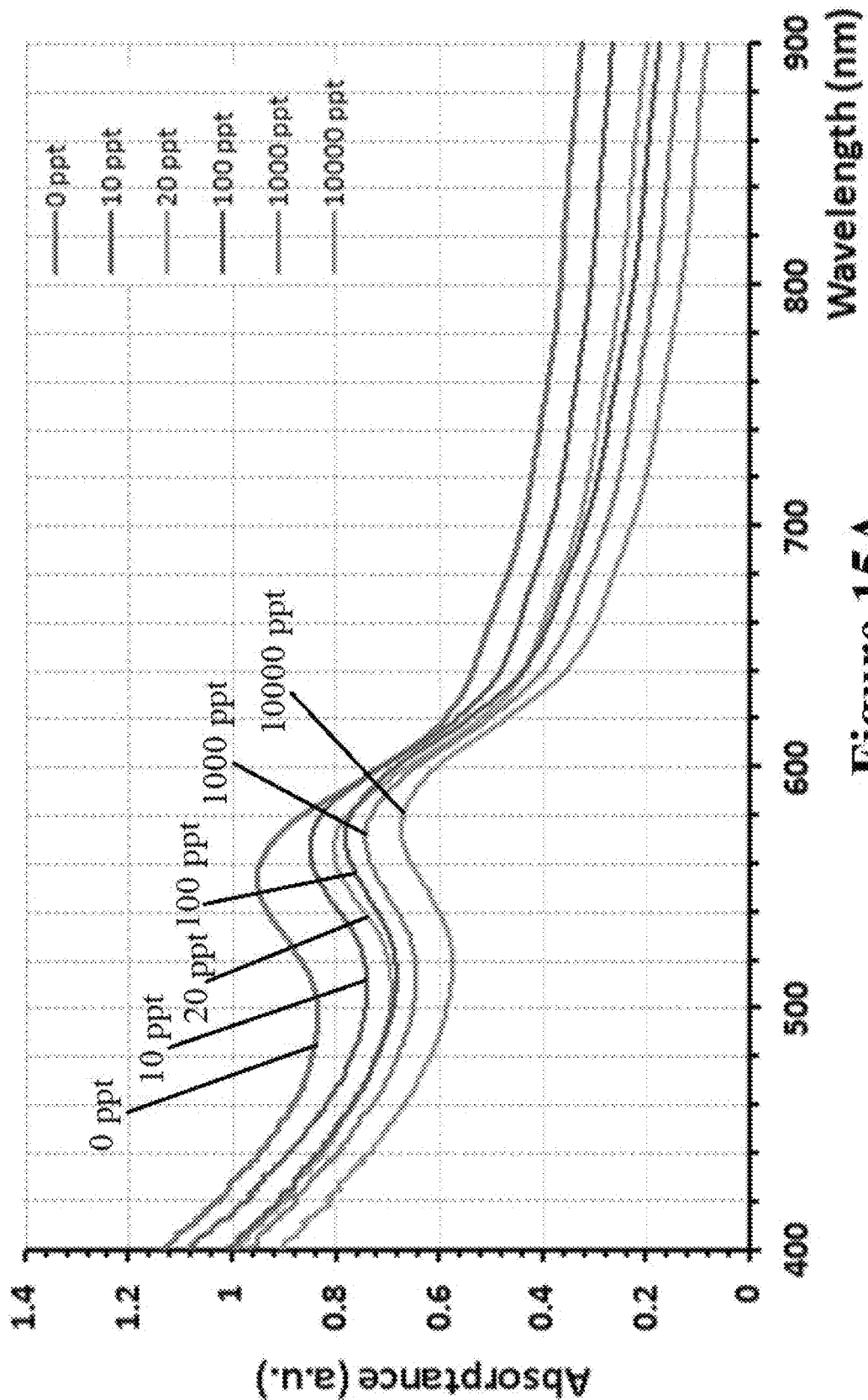
FIG. 15A shows vis-NIR spectra of a sensor at analyte concentrations of from 10 ppt to 10,000 ppt in accordance with an exemplary embodiment of the present invention.
Figure 15B:
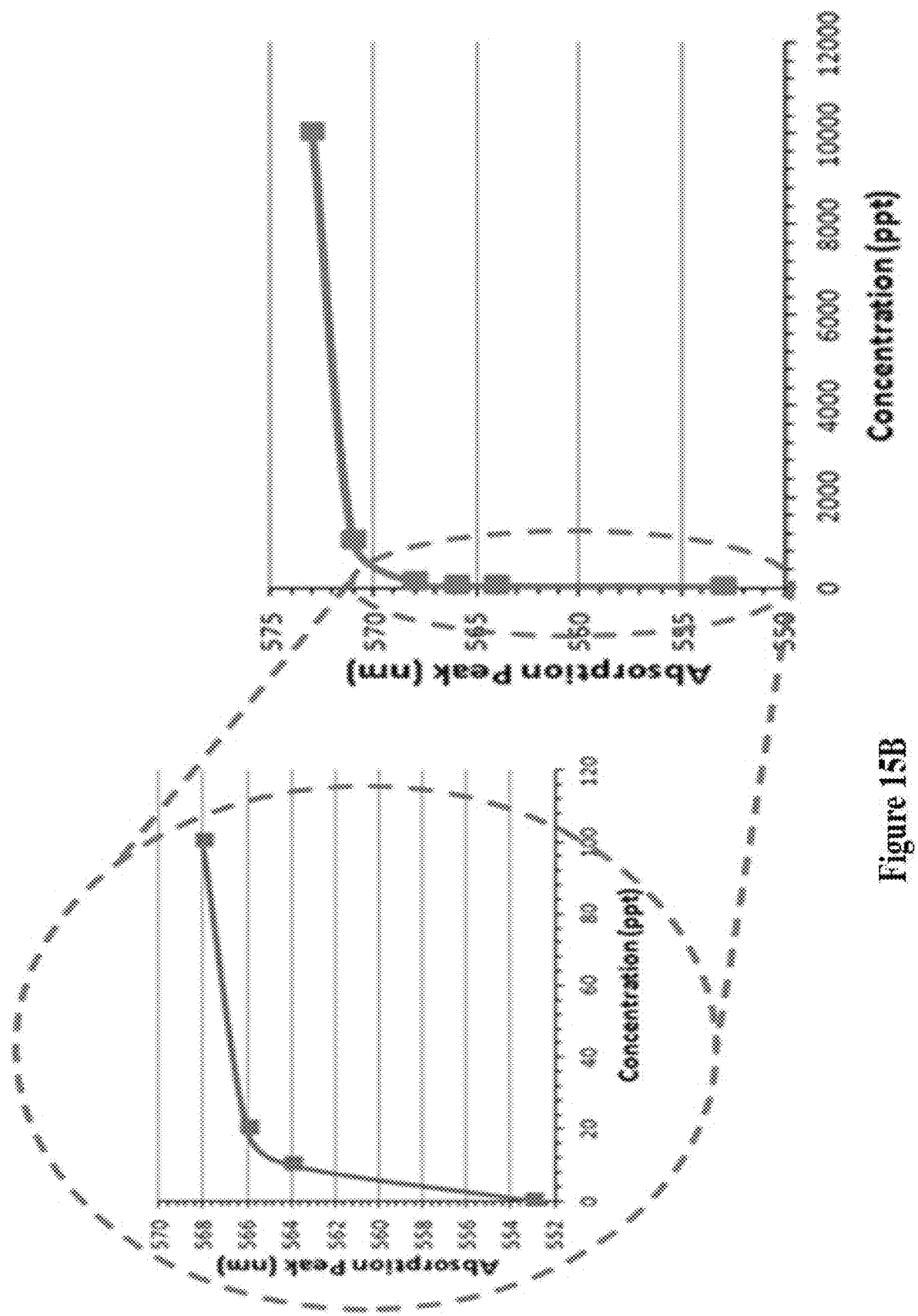
FIG. 15B shows a calibration curve in the range from 0 ppt to 10,000 ppt in accordance with an exemplary embodiment of the present invention.

Trace detection of PFOA was successfully demonstrated using the PFOA-imprinted photonic crystal sensor Due to the low surface energy of the fluoro-containing sensor, a suitable amount of methanol was added to the PFOA water solution for improved analyte/sensor affinity. During measurement, 5-10 µL of PFOA solution was pipetted over a 10×10 mm sensing area After incubating for 10 seconds, the solution on the sensor was wiped away. After the solvent evaporated, the vis-NIR spectrum of the sensor was measured and the absorption peaks and corresponding wavelengths were identified. PFOA solutions with PFOA concentrations of 10 ppt, 20 ppt, 100 ppt, 1000 ppt and 10 ppb were prepared using a mixed solvent of water/methanol (1/4, v/v) Extensive sensor evaluation, including other test solutions with reduced methanol content (or other environment-friendly solvents such as ethanol and IPA) may be performed as well. The sensors were fabricated using colloid crystal templates of 300 nm silica nanoparticles. FIG. 15A shows vis-NIR spectra of the sensor at different concentrations from 10 ppt to 10,000 ppt. FIG. 15A shows Vis-NIR spectra of the molecularly imprinted sensor at different PFOA concentrations from 10 ppt to 10,000 ppt. It can be clearly seen that the absorption peak red-shifts with increasing PFOA concentration, as indicated in Table 1 below. Table 1 lists the absorption peak wavelengths at different PFOA concentrations. FIG. 15B shows a calibration curve in the range from 0 ppt to 10,000 ppt.

TABLE 1

| PFOA Concentration (ppt) | Peak Wavelength (nm) |
| --- | --- |
| 0 | 553 |
| 10 | 564 |
| 20 | 566 |
| 100 | 568 |
| 1,000 | 571 |
| 10,000 | 573 |

Figure 16:
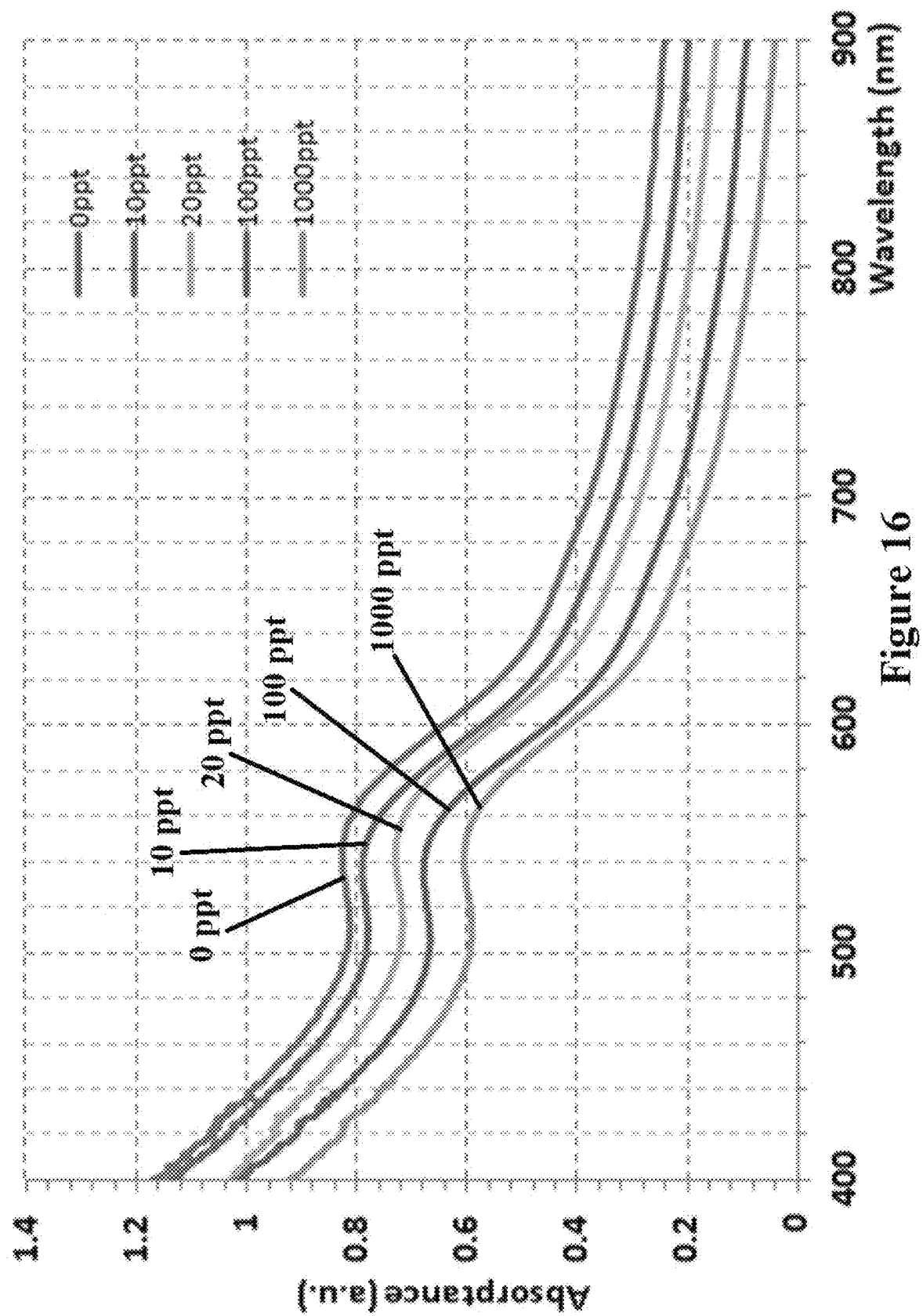
FIG. 16 shows vis-NIR spectra of non-molecularly imprinted sensors at PFOA concentrations of from 10 ppt to 1,000 ppt in accordance with an exemplary embodiment of the present invention.

For comparison, non-molecularly imprinted sensors were fabricated and evaluated. The vis-NIR spectra of the sensor at different PFOA concentrations from 10 ppt to 1,000 ppt are given in FIG. 16. The absorption peak wavelengths at different PFOA concentrations are listed in Table 2. As expected, no absorption peak shift was observed for the non-molecularly imprinted sensor in the detected concentration range of PFOA.

TABLE 2

| PFOA Concentration (ppt) | Peak Wavelength (nm) |
| --- | --- |
| 0 | 544 |
| 10 | 544 |
| 20 | 543 |
| 100 | 543 |
| 1000 | 544 |

Various embodiments of the invention can provide a facile technology for fabricating a highly-ordered 3D colloidal photonic crystal array that consistently produces very good optical signals. Multiple highly-ordered multi-layered colloid crystal templates were prepared on a glass slide using this two-phase self-assembly process. Maximum thickness of the template was approximately 3 µm, with a uniform area larger than 3 cm². This crystal template was used to create a 3D-ordered and interconnected macroporous MIP structure which was utilized to detect PFOA molecules inside a solution. Polymer photonic crystal sensors successfully detected the 10 ppt target molecule solutions of PFOA by showing excellent Bragg peak shift (over 10 nm). MIP-based sensors could function similarly to pH paper and provide a promising alternative for rapid monitoring of PFOA levels on the spot. The MW sensor has sufficient specificity, and it can be used in arrays of optical sensors in which each individual sensor can detect a different PFAS.

Referring back to FIG. 2, various embodiments of the invention provide a sensing device 300 comprising a working sensor 100 as described above. In preferred embodiments, sensing device 300 further includes a reference sensor 200 that is the same as the working sensor 100 except that (1) the reference sensor 200 does not include the cavities 130 as those in the working sensor 100, and (2) voids 220's size of the reference sensor 200 is different from (bigger than or smaller than) voids 120's size of the working sensor 100.

Figure 17:
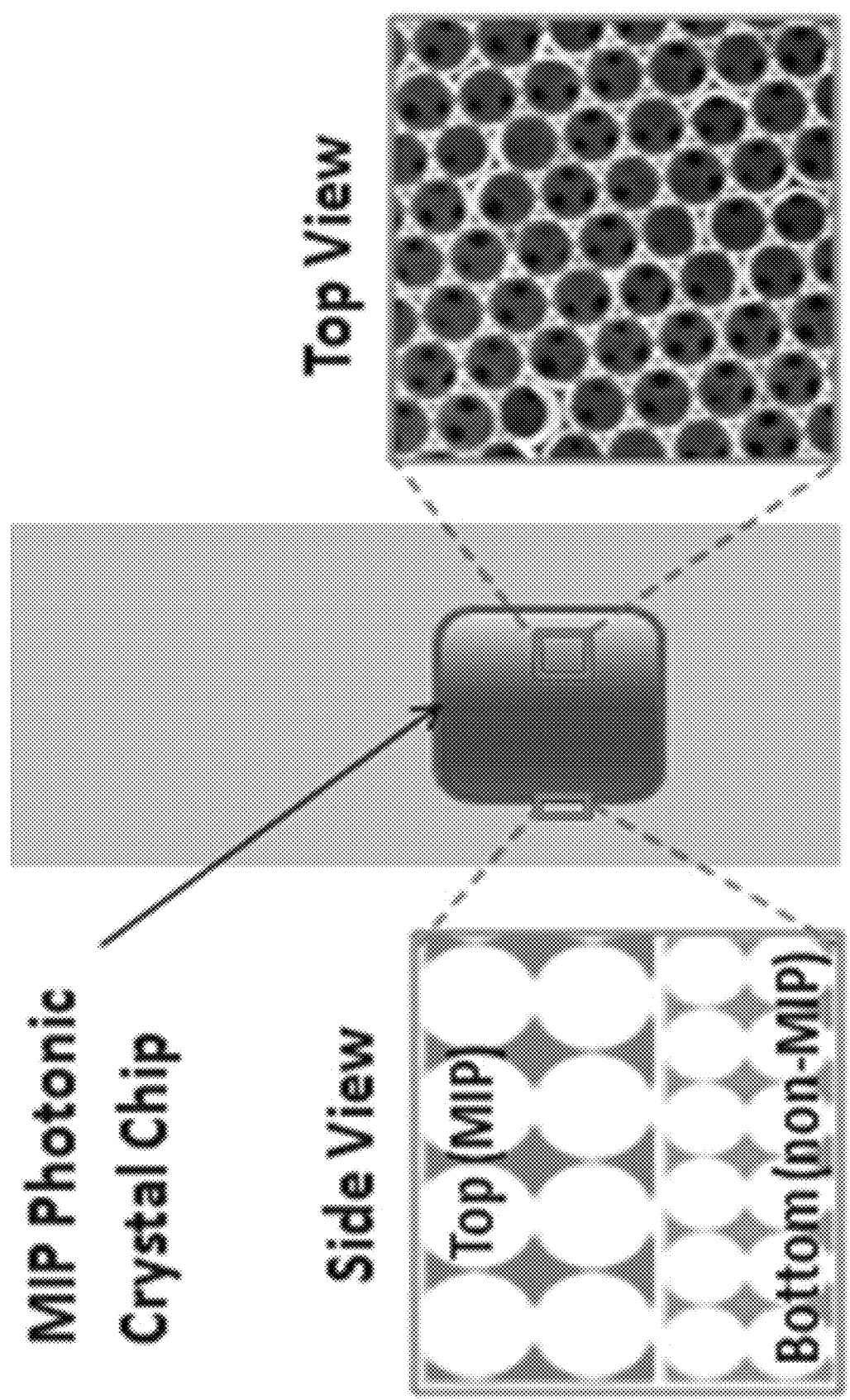
FIG. 17 shows a chip assembled onto a clear microscope slide support in accordance with an exemplary embodiment of the present invention.

In representative and still exemplary embodiments, the present invention provides a bi-layered molecularly imprinted photonic crystal sensor with built-in standard. For example, a bi-layered MIP photonic crystal-based sensing device can achieve the goal of fast field trace detection of atrazine in water. The photonic crystal sensing chip includes two layers of 3D-ordered interconnected macroporous structure. The top layer (MIP layer) may be molecularly imprinted and have a longer periodical length (i a longer absorption peak wavelength) while the bottom layer will be non-imprinted (non-MIP) and have a shorter periodical length (i.e. a shorter absorption peak wavelength). For ease of use, the chip may be assembled onto a clear microscope slide support, as shown in FIG. 17. In the MIP layer, numerous nanocavities derived from atrazine molecular imprinting (MIP) may be distributed in the thin walls of the ordered macro-pores (inverse polymer opal). During detection, the nanocavities will recognize atrazine molecules with high specificity and induce a refractive index change of the ordered structure, leading to an absorption peak wavelength shift. The peak shift can be detected using a handheld UV-Vis spectrometer, which can be correlated with the concentration of atrazine in water. The non-MIP bottom layer cannot bind to the analyte molecules, so its absorption peak wavelength will not be affected by changing of the analyte concentration. The absorption peak from the non-MIP layer can be used as an internal standard to calibrate the peak shift of the sensing MIP layer. The embodiment thus provides a bi-layered MIP sensing platform with built-in standard (reference peak) to eliminate non-molecular binding induced effects.

Figure 18:
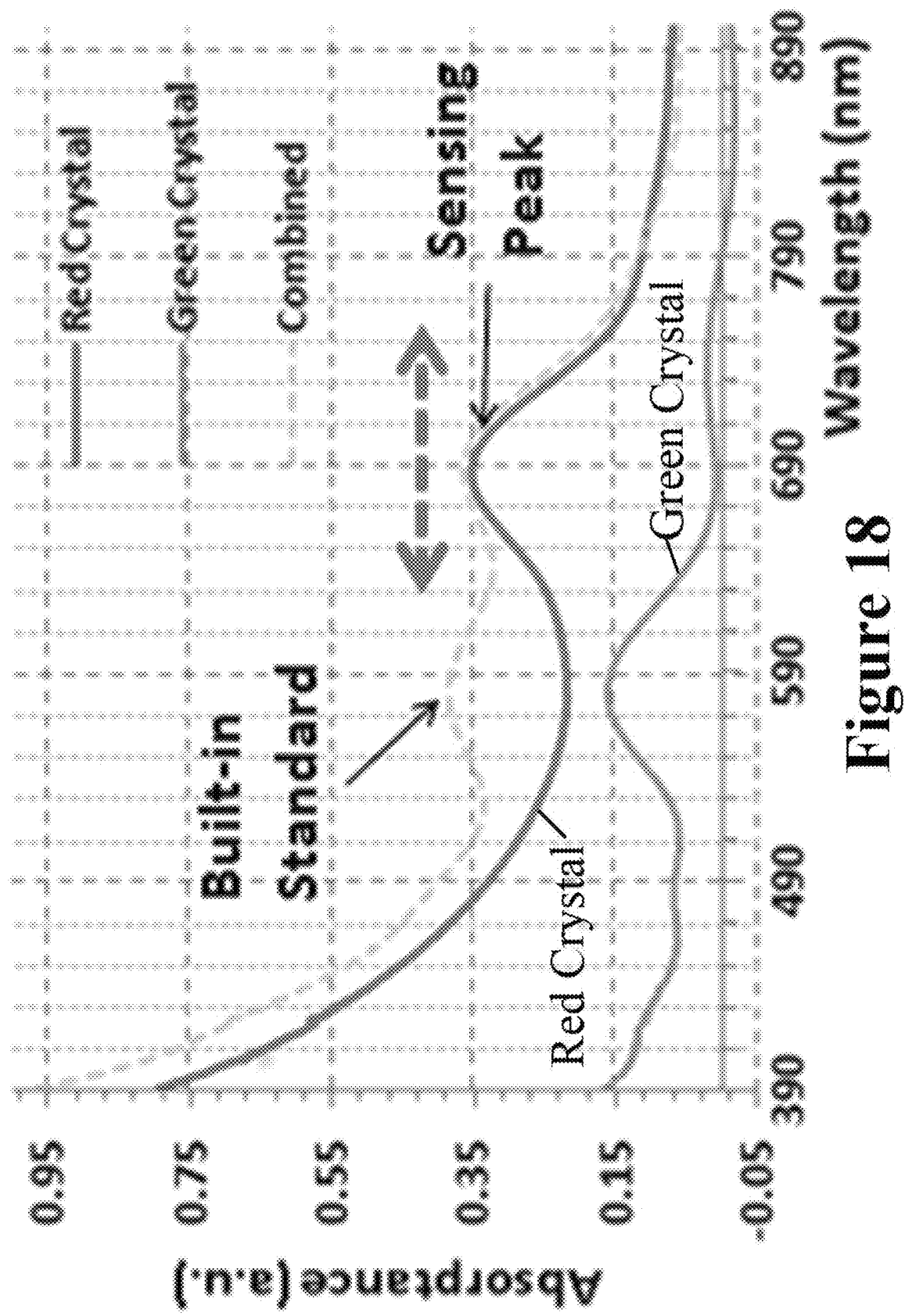
FIG. 18 shows the UV-Vis spectra of colloid crystals independently (Green and Red) and when they are combined (yellow) in accordance with an exemplary embodiment of the present invention.

During measurement, the sensing chip may be brought into contact with the analyte solution. The analyte molecules will bind to the MIP nanocavities, leading to absorption peak shift. Besides the peak shift induced by the binding of the analyte molecule other factors might also affect peak shift. Saturation of the polymer matrix by the solvent might induce swelling to some extent Additionally, variations in the surrounding temperature may cause hydrogel contraction/expansion during the measurement. These non-molecular binding factors may also affect the absorption peak shift in the non-MIP layer. With this built-in standard, the peak shift effects from sources besides molecular binding can be eliminated FIG. 18 shows the UV-Vis spectra of colloid crystals independently (Green and Red) and when combined (yellow). The sensor measures absorption peak wavelength shift instead of peak intensity change. Besides Bragg diffraction, peak intensity is also affected by other experimental factors such as substrate scattering, surface roughness, spectrometer settings, ambient light, etc. However, the absorption peak position is only determined by the periodical length of the inverse opal structure and the refractive index change of the hydrogel induced by the nanocavities binding template molecules. The other experimental factors mentioned above (which change peak intensity) won't change peak position.

There is no labeling process involved with the test process. Conventional immunoassays use labeled antibodies for the detection of biomolecules, which are time-consuming to create and expensive Label-free detectors for biomolecules have drawn increasing interest from researchers in the fields of proteomics, clinical diagnostics, and environmental monitoring. In label-free sensors, target molecules are detected in their natural forms without any labeling process. The sensor of the invention has the advantage of eliminating time-consuming and expensive labeling steps, as well as allowing for kinetic measurement of molecular interactions. As artificial antibodies, molecularly imprinted polymers have high affinity for their template molecules. A limit of detection as low as $10^{-16}$ M of atrazine in water (equivalent to 0.0215 ppt) has been demonstrated. The high degree of specificity stems from the high affinity of molecularly imprinted nano-cavities.

Molecularly imprinted photonic polymers may be fabricated using the above procedure with some modifications. In order to make a bi-layered sensor, a non-MIP reference layer will first be made on a PMMA support, followed by a MIP sensing layer on the reference layer.

Using a bi-layer MIP sensor, the UV-vis spectrum of an atrazine solution may show two absorption peaks with a reference peak at $\lambda_r$ and a sensing peak at $\lambda_s$. Before measurement, the sensor can be calibrated with the solvent used to make the atrazine solution as the starting point, which gives a reference peak position at $\lambda_{r0}$ and a sensing peak position at $\lambda_{s0}$. During measurement of test solution #1 with atrazine concentration of $C_1$, its UV-Vis spectrum will show a reference peak position at $\lambda_{r1}$ and a sensing peak position at $\lambda_{s1}$. The absorption peak shift $\Delta\lambda_1$ can be calculated using the following equation.

$$\Delta\lambda_1 = (\lambda_{s1} - \lambda_{r0}) - (\lambda_{s0} - \lambda_{r0}) \quad (2)$$

For test solution #n with atrazine concentration of $C_n$, its UV-Vis spectrum will show a reference peak position at $\lambda_{rn}$ and a sensing peak position at $\lambda_{sn}$. The absorption peak shift $\Delta\lambda_n$ can be expressed as follows:

$$\Delta\lambda_n = (\lambda_{sn} - \lambda_{rn}) - (\lambda_{s0} - \lambda_{r0}) \quad (3)$$

With the known concentrations ($C_n$) of test solutions and their corresponding absorption peak shift ($\Delta\lambda_n$), a calibration curve can be plotted. From the calibration curve, the limit of detection, sensitivity, and dynamic range of the sensor can be deduced. In order to determine the atrazine concentration of an unknown solution, the solution will be applied on a sensor with a known calibration curve. The UV-Vis spectrum of the sensor will be measured and its atrazine concentration can be determined from the absorption peak shift.

In the foregoing specification, embodiments of the present invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicant to be the scope of the invention, is the literal and equivalent scope of the set of claims that issue from this application, in the specific form in which such claims issue, including any subsequent correction.

The invention claimed is:

1. A sensing device comprising a working sensor for detecting an analyte containing a non-metallic element, wherein the working sensor comprises a sensing body including a 3D array of voids each having a void internal wall;
   wherein at least a part of the voids are interconnected to each other and are configured to expose to said analyte, and admit said analyte into said at least a part of the voids;
   wherein void internal walls of said at least a part of the voids have cavities each having a cavity internal wall;
   wherein each of the cavities has a shape that is complementary to a shape of the analyte;
   wherein the cavity internal wall is made from a material containing said non-metallic element;
   wherein the sensing body, the void internal walls, and the cavity internal walls are all made from a same material containing said non-metallic element;
   wherein said same material comprises a polymer prepared from photo polymerization and/or thermal polymerization using monomers containing said non-metallic element;
   wherein said same material is prepared from a pre-polymerization composition comprising said monomers containing said non-metallic element, the analyte containing said non-metallic element, and an optional cross-linking agent; and
   wherein the pre-polymerization composition comprises template/analyte molecule perfluorooctanoic acid (PFOA); said monomers including 2-(trifluoromethyl) acrylic acid (TFMAA), 2-(difluoromethyl) acrylic acid (DFMAA), and/or 2-(monofluoromethyl) acrylic acid (MFMAA); and cross-linking agent ethylene glycol dimethacrylate (EGDMA) that utilizes an interaction between the non-metallic elements.

2. The sensing device according to claim 1, wherein the non-metallic element is selected from F, Cl, Br, I, O, S, Se, Te, N, P, As, Sb, B, C, H, or any combination thereof.

3. The sensing device according to claim 1, wherein the non-metallic element comprises F.

4. The sensing device according to claim 1, wherein the interaction between the non-metallic elements is selected from fluorine-fluorine interactions, electrostatic attraction, and associated weak interactions.

5. The sensing device according to claim 1, wherein the pre-polymerization composition further comprises monomers that do not contain said non-metallic element.

6. The sensing device according to claim 1, wherein the array of voids is a 3D array of voids formed by removing a colloidal crystal from a solid body into which the colloidal crystal is incorporated and integrated.

7. The sensing device according to claim 6, wherein the colloidal crystal includes silica nanoparticles, polystyrene nanoparticles, or any combination thereof.

8. The sensing device according to claim 6, wherein the 3D array of voids is formed by stacking a number of 2D array of voids, and a height of the stack of 2D array of voids, or a thickness of the 3D array of voids, is approximately 2-10 μm.

9. The sensing device according to claim 8, wherein the 3D array of voids is formed by stacking 5-20 layers of 2D array of voids.

10. The sensing device according to claim 8, wherein the 2D array of voids has a uniform area of 0.01-4 cm$^2$.

11. The sensing device according to claim 6, wherein the size of the voids is in the range of from 180 nm to 400 nm.

12. The sensing device according to claim 1, wherein the sensing body is deposited on a polymer plate.

13. The sensing device according to claim 1, wherein a binding of the analytes to the cavities induces or triggers a detectable variation of the optical property of the 3D array of voids, including a spectrum of light that is transmitted through, reflected from, and/or diffracted from the 3D array of voids; and a degree of the detectable variation is correlated with the amount of the analytes bound to the cavities.

14. A sensing device comprising a working sensor for detecting an analyte containing a non-metallic element, wherein the working sensor comprises a sensing body including a 3D array of voids each having a void internal wall;
   wherein at least a part of the voids are interconnected to each other and are configured to expose to said analyte, and admit said analyte into said at least a part of the voids;
   wherein void internal walls of said at least a part of the voids have cavities each having a cavity internal wall;
   wherein each of the cavities has a shape that is complementary to a shape of the analyte; wherein the cavity internal wall is made from a material containing said non-metallic element;
   wherein the sensing device further comprises a reference sensor that also comprises a sensing body including a 3D array of voids each having a void internal wall;
   wherein at least a part of the voids in the reference sensor are also interconnected to each other and are configured to expose to said analyte, and admit said analyte into said at least a part of the voids;
   wherein void internal walls of said at least a part of the voids in the reference sensor, unlike those in the working sensor, do not have cavities each having a cavity internal wall and a shape that is complementary to a shape of the analyte; and
   wherein the voids' size of the reference sensor is different from that of the working sensor.

15. A method of measuring an analyte containing a nonmetallic element, comprising:
   (i) providing the sensing device according to claim 1,
   (ii) contacting a sample of the analyte with the working sensor,
   (iii) binding the analyte to the cavities and inducing or triggering a detectable variation of the optical property of the 3D array of voids, including a spectrum of light that is transmitted through, reflected from, and/or diffracted from the 3D array of voids, and
   (iv) correlating a degree of the detectable variation to an amount of the analytes bound to the cavities.

16. The method according to claim 15, wherein the analyte contains F, C, and/or H.

17. The method according to claim 16, wherein the analyte is selected from fluorinated chemicals.

18. A method of measuring an analyte containing a nonmetallic element, comprising:
   (i) providing the sensing device according to claim 14,
   (ii) contacting a sample of the analyte with the working sensor,
   (iii) binding the analyte to the cavities and inducing or triggering a detectable variation of the optical property of the 3D array of voids, including a spectrum of light that is transmitted through, reflected from, and/or diffracted from the 3D array of voids, and
   (iv) correlating a degree of the detectable variation to an amount of the analytes bound to the cavities.

\* \* \* \* \*